(12) United States Patent
Jirstrom

(10) Patent No.: US 9,354,232 B2
(45) Date of Patent: May 31, 2016

(54) PODXL IN BLADDER CANCER

(71) Applicant: Atlas Antibodies AB, Stockholm (SE)

(72) Inventor: Karin Jirstrom, Limhamn (SE)

(73) Assignee: Atlas Antibodies AB, Stockholm (SE)

( * ) Notice: Subject to any disclaimer, the term of this patent is extended or adjusted under 35 U.S.C. 154(b) by 0 days.

(21) Appl. No.: 14/646,918

(22) PCT Filed: Dec. 11, 2013

(86) PCT No.: PCT/EP2013/076179
§ 371 (c)(1),
(2) Date: May 22, 2015

(87) PCT Pub. No.: WO2014/095508
PCT Pub. Date: Jun. 26, 2014

(65) Prior Publication Data
US 2015/0309030 A1    Oct. 29, 2015

Related U.S. Application Data

(60) Provisional application No. 61/739,812, filed on Dec. 20, 2012.

(30) Foreign Application Priority Data

Dec. 20, 2012    (EP) .................................... 12198437

(51) Int. Cl.
*G01N 33/53* (2006.01)
*G01N 33/574* (2006.01)
*G01N 33/50* (2006.01)
*A61K 39/04* (2006.01)
*A61N 5/10* (2006.01)

(52) U.S. Cl.
CPC .......... *G01N 33/57407* (2013.01); *A61K 39/04* (2013.01); *A61N 5/10* (2013.01); *G01N 33/5091* (2013.01); *G01N 33/574* (2013.01); *G01N 33/57434* (2013.01); *G01N 2333/705* (2013.01); *G01N 2800/52* (2013.01)

(58) Field of Classification Search
None
See application file for complete search history.

(56) References Cited

U.S. PATENT DOCUMENTS

2006/0294607 A1* 12/2006 Fitzhugh .............. C07K 14/705
800/14

FOREIGN PATENT DOCUMENTS

EP          2452950 A1    5/2012
WO     WO 98/12564 A1    3/1998

OTHER PUBLICATIONS

Fradet et al. "Strategies of Chemoprevention Based on Antigenic and Molecular Markers of Early and Premalignant Lesions of the Bladder", *J. Cellular Biochemistry* Suppl. 161:85-92 (1992).
Weber et al. "Multimodal treatment strategies for locally advanced rectal cancer", *Expert Rev. of Anticancer Ther.* 12(4):481-494 (2012).
International Search Report corresponding to International Application No. PCT/EP2013/076179 mailed Feb. 12, 2014.
International Preliminary Report on Patentability corresponding to International Application No. PCT/EP2013/076179 mailed Oct. 10, 2014.

* cited by examiner

*Primary Examiner* — Sean Aeder
(74) *Attorney, Agent, or Firm* — Myers Bigel & Sibley, P.A.

(57) ABSTRACT

There is provided a method for determining whether a mammalian subject having a bladder cancer belongs to a first or a second group, wherein the prognosis of subjects of the second group is worse than the prognosis of subjects of the first group, comprising the steps of: a) evaluating an amount of PODXL in at least part of a sample earlier obtained from the subject and determining a sample value corresponding to the evaluated amount; b) comparing said sample value with a predetermined reference value; and if said sample value is higher than said reference value, c1) concluding that the subject belongs to the second group; and if said sample value is lower than or equal to said reference value, c2) concluding that the subject belongs to the first group.

21 Claims, 7 Drawing Sheets

PODXL IN BLADDER CANCER

STATEMENT OF PRIORITY

This application is a 35 U.S.C. §371 national phase application of PCT Application No. PCT/EP2013/076179 filed Dec. 11, 2013, which claims priority to European Application No. 12198437.1 filed Dec. 20, 2012 and also claims the benefit of U.S. Provisional Application Ser. No. 61/739,812, filed Dec. 20, 2012, the entire contents of each of which is incorporated by reference herein.

STATEMENT REGARDING ELECTRONIC FILING OF A SEQUENCE LISTING

A Sequence Listing in ASCII text format, submitted under 37 C.F.R. §1.821, entitled 9868-40TS_ST25.txt, 12,907 bytes in size, generated on May 18, 2015 and filed via EFS-Web, is provided in lieu of a paper copy. The Sequence Listing is incorporated herein by reference into the specification for its disclosures.

TECHNICAL FIELD

The present disclosure relates to the field of bladder cancer and in particular to prognosis and treatment thereof. Further, it relates to means useful in the establishment of a prognosis or treatment prediction.

BACKGROUND

Cancer

Cancer is one of the most common diseases, and a major cause of death in the western world. In general, incidence rates increase with age for most forms of cancer. As human populations continue to live longer, due to an increase of the general health status, cancer may affect an increasing number of individuals. The cause of most common cancer types is still largely unknown, although there is an increasing body of knowledge providing a link between environmental factors (dietary, tobacco smoke, UV radiation etc) as well as genetic factors (germ line mutations in "cancer genes" such as p53, APC, BRCA1, XP etc) and the risk for development of cancer.

No definition of cancer is entirely satisfactory from a cell biological point of view, despite the fact that cancer is essentially a cellular disease and defined as a transformed cell population with net cell growth and anti-social behavior. Malignant transformation represents the transition to a malignant phenotype based on irreversible genetic alterations. Although this has not been formally proven, malignant transformation is believed to take place in one cell, from which a subsequently developed tumor originates (the "clonality of cancer" dogma). Carcinogenesis is the process by which cancer is generated and is generally accepted to include multiple events that ultimately lead to growth of a malignant tumor. This multi-step process includes several rate-limiting steps, such as addition of mutations and possibly also epigenetic events, leading to formation of cancer following stages of precancerous proliferation. The stepwise changes involve accumulation of errors (mutations) in vital regulatory pathways that determine cell division, asocial behavior and cell death. Each of these changes may provide a selective Darwinian growth advantage compared to surrounding cells, resulting in a net growth of the tumor cell population. A malignant tumor does not only necessarily consist of the transformed tumor cells themselves but also surrounding normal cells, which act as a supportive stroma. This recruited cancer stroma consists of connective tissue, blood vessels and various other normal cells, e.g., inflammatory cells, which act in concert to supply the transformed tumor cells with signals necessary for continued tumor growth.

The most common forms of cancer arise in somatic cells and are predominantly of epithelial origin, e.g., prostate, breast, colon, urothelium and skin, followed by cancers originating from the hematopoetic lineage, e.g., leukemia and lymphoma, neuroectoderm, e.g., malignant gliomas, and soft tissue tumors, e.g., sarcomas.

Cancer Diagnostics and Prognostics

Microscopic evaluation of biopsy material from suspected tumors remains the golden standard for cancer diagnostics. To obtain a firm diagnosis, the tumor tissue is fixated in formalin, histo-processed and paraffin embedded. From the resulting paraffin block, tissue sections can be produced and stained using both histochemical, i.e., hematoxylin-eosin staining, and immunohistochemical (IHC) methods. The surgical specimen is then evaluated with pathology techniques, including gross and microscopic analysis. This analysis often forms the basis for assigning a specific diagnosis, i.e., classifying the tumor type and grading the degree of malignancy, of a tumor.

Malignant tumors can be categorized into several stages according to classification schemes specific for each cancer type. The most common classification system for solid tumors is the tumor-node-metastasis (TNM) staging system. The T stage describes the local extent of the primary tumor, i.e., how far the tumor has invaded and imposed growth into surrounding tissues, whereas the N stage and M stage describe how the tumor has developed metastases, with the N stage describing spread of tumor to lymph nodes and the M stage describing growth of tumor in other distant organs. Early stages include: T0-1, N0, M0, representing localized tumors with negative lymph nodes. More advanced stages include: T2-4, N0, M0, localized tumors with more widespread growth and T1-4, N1-3, M0, tumors that have metastasized to lymph nodes and T1-4, N1-3, M1, tumors with a metastasis detected in a distant organ. Staging of tumors is often based on several forms of examination, including surgical, radiological and histopathological analyses. In addition to staging, for most tumor types there is also a classification system to grade the level of malignancy. The grading systems rely on morphological assessment of a tumor tissue sample and are based on the microscopic features found in a given tumor. These grading systems may be based on the degree of differentiation, proliferation and atypical appearance of the tumor cells. Examples of generally employed grading systems include Gleason grading for prostatic carcinomas and the Nottingham Histological Grade (NHG) grading for breast carcinomas.

Accurate staging and grading is often crucial for a correct diagnosis and may provide an instrument to predict a prognosis. The diagnostic and prognostic information for a specific tumor is taken into account when an adequate therapeutic strategy for a given cancer patient is determined.

A commonly used method, in addition to histochemical staining of tissue sections, to obtain more information regarding a tumor is immunohistochemical staining. IHC allows for the detection of protein expression patterns in tissues and cells using specific antibodies. The use of IHC in clinical diagnostics allows for the detection of immunoreactivity in different cell populations, in addition to the information regarding tissue architecture and cellular morphology that is assessed from the histochemically stained tumor tissue section. IHC can be involved in supporting the accurate diagnosis, including staging and grading, of a primary tumor as well as in the diagnostics of metastases of unknown origin. The most commonly used antibodies in clinical practice today include antibodies against cell type "specific" proteins, e.g., PSA (prostate), MelanA (melanocytes) and Thyroglobulin (thyroid gland), and antibodies recognizing intermediate filaments (epithelial, mesenchymal, glial), cluster of differentiation (CD) antigens (hematopoetic, sub-classification of lympoid cells) and markers of malignant potential, e.g., Ki67 (proliferation), p53 (commonly mutated tumor suppressor gene) and HER-2 (growth factor receptor).

Aside from IHC, the use of in situ hybridization for detecting gene amplification and gene sequencing for mutation analysis are evolving technologies within cancer diagnostics. In addition, global analysis of transcripts, proteins or metabolites adds relevant information. However, most of these analyses still represent basic research and have yet to be evaluated and standardized for the use in clinical medicine.

Bladder Cancer

World wide, bladder cancer is the ninth most common form of cancer. Bladder cancer is more common in men than in women; of a total of approximately 336 000 new cases yearly, about 260 000 occur in men and about 76 000 in women. The incidence varies widely between countries, and also the type of cancer. In the industrialized world, the most common type of bladder cancer is urothelial carcinoma (appr. 90% of cases). In developing countries, squamous cell carcinomas are most common, although this type only contributes to a few percent of bladder cancers in the western world. The world wide incidence of urothelial cancer is approximately 3.3% of all new cancers, and nearly 150 000 deaths per year can be contributed to this disease. The risk of developing bladder cancer increases with age and the median age at diagnosis is 70 years for men and women combined.

Today, the largest known risk factor for bladder cancer is use of tobacco, particularly cigarette smoking. Other risk factors include flue gases from coal combustion and ionizing radiation. Genetic factors that contribute to the disease have as yet not been identified.

Bladder Cancer Diagnostics

Screening of patients for early detection of bladder cancer is generally not recommended today. A few markers have been approved by the FDA for use in urine screening, such as BTA-Stat and NMP22, however, these have not proven to be reliable enough. Blood in the urine is a common first symptom of bladder cancer, but is not always present. Other symptoms may be pain across the pubic bone, frequent urination and stinging, or symptoms similar to an ordinary bladder infection. When a patient presents with symptoms that may indicate bladder cancer, a CT-urography is performed. After the CT-urography, a cystoscopic examination is made in which a flexible tube is introduced into the bladder through the urethra. The tube is bearing a camera and a tool to remove tissue from dubious lesions. If tumor tissue is found, resection of the bladder may be performed to remove all traces of tumor, and multiple biopsies may also be taken from the mucous membrane, in a so called mapping procedure.

The cytological diagnosis of grade 1 tumors may be difficult, and the diagnostic accuracy is only about 50% in these cases today. Confounding factors may include e.g. inflammation.

Treatment of Bladder Cancer

Early detection and surgery with excision of the tumor may be of critical importance for a successful treatment. Superficial tumors can be surgically removed or "shaved off", but for invasive tumors, more radical surgery may be needed, whereby the standard approach today is radical cystectomy/removal of the bladder, with or without chemotherapy. Bladder cancer typically metastasizes to regional lymph nodes, but distant metastases in the lung, skin, liver and bones are not unusual.

At the time of diagnosis, a transurethral resection of the bladder (TUR-B) is usually performed, which in itself may be a curative treatment for non-invasive bladder cancer. However, in cases with a high risk of recurrence, patients may be given chemotherapy or *Bacillus* Calmette-Guerin (BCG) as instillation treatment. In cases with multifocal tumors or frequent recurrences, intravesical instillation during a longer time period may be considered.

Cancer in situ of the bladder is currently treated by BCG instillation. If the tumor fails to respond to treatment, a cystectomy may be performed where all or part of the bladder is removed.

Muscle-invasive bladder cancer, stage T2-T4a, is currently treated by radical cystectomy and lymph node dissection of the small pelvis. Neoadjuvant or adjuvant chemotherapy can also be considered for aggressive tumors. According to current protocols in Sweden, adjuvant chemotherapy after cystectomy is only recommended to patients enrolled in controlled clinical trials. For inoperable patients, radiation treatment may be given, possibly in combination with chemotherapy.

Prognostics and Treatment Predictive Factors

Prognostic information can be obtained from tumor grade. Urothelial tumors are divided into five grades according to WHO standards: Papillomas, LMP (low malignant potential), and cancer grade 1-3. This grading is based on histological criteria and cell morphology. In grade 1, the tumor cells are well differentiated and grow mainly organized, in grade 2, the tumor cells are moderately differentiated and have a mainly unorganized structure, and in grade 3, the tumor cells are poorly differentiated.

Urothelial tumors are classified according to the TNM staging system. TIS represents tumor (or cancer) in situ. Cancer in situ of the bladder is a flat, low differentiated tumor (grade 3) that occurs in three different forms:

Primary: TIS without other tumor growth present;

Secondary: TIS discovered during follow-up after treatment of an exophytic tumor; and Concomitant: TIS with other tumor growth present.

Stage Ta is a non-invasive tumor, and in the T1-stage, the tumor has invaded the lamina propria (the subepithelial connective tissue). In stage T2, the tumor invades muscle, in stage T3, the tumor invades perivesical tissue, and in stage T4, the tumor invades other organs.

Approximately 70% of bladder cancers are either entirely superficial tumors or only invading as far as the lamina propria (stage Ta or T1). Local recurrence of these tumors are common (50-70% recurrence rate), and patients normally need to be followed regularly with cystoscopic examinations to detect any recurrences at an early stage. This is a costly procedure causing great discomfort for the patient. These superficial tumors seldom progress to a more aggressive form, but in about 10-15% of cases they do. Among these tumors, three risk groups have been suggested by the European Association of Urology (EAU), namely:

Low risk tumors: tumors that are LMP, stage Ta tumors of grade 1 or tumors less than 3 cm in size;

Medium risk tumors: stage Ta tumors of grade 1 or 2 and more than 3 cm in size; and High risk tumors: stage Ta tumors of grade 3, stage T1 tumors, or Tis tumors.

The high risk tumors have an increased tendency to progress to more aggressive forms, and patients with high risk tumors will have to be closer monitored than those with low or medium risk tumors.

The least malignant tumors, Ta and T1, are associated with a relatively favorable outcome, and a current five-year survival rate of 90 and 75%, respectively. More invasive tumors have a less favorable prognosis with a five-year survival rate of approximately 60% for stage T2 and 35% for stage T3. Tumors with metastases (N1-4 and/or M1) have an even worse prognosis.

Cisplatin-based chemotherapy has proven to be efficient in advanced bladder cancer, with response rates of approx. 30% for single-agent treatment and more than 50% for combination treatment with other agents. However, long-term survival is currently low, only 10-15% of patients survive up to 5 years, and few molecular markers have proven to be of value in prediction of treatment response.

Fradet et al. (Journal of Cellular Biochemistry, Supplement 161:85-92 (1992)) and WO 98/12564 disclose various antigens and their role in bladder cancer. One of the antigens is the gp200 surface antigen 19A211, which is part of the family of carcinoembryonic antigens (CEA). "gp200" indicate that it is a glycoprotein having a molecular weigh of 200 kD. However, the gp200 surface antigen 19A211 is neither identical nor related to antigen PODXL, which was sometimes referred to gp200 in the past.

SUMMARY

There is an object of the present invention to provide improvements related to bladder cancer prognosis and treatment.

The following is a non-limiting and itemized listing of embodiments of the present disclosure, presented for the purpose of providing various features and combinations provided by the invention in certain of its aspects.

1. Method for determining whether a mammalian subject having a bladder cancer belongs to a first or a second group, wherein the prognosis of subjects of the second group is worse than the prognosis of subjects of the first group, comprising the steps of:
   a) evaluating an amount of PODXL in at least part of a sample earlier obtained from the subject and determining a sample value corresponding to the evaluated amount;
   b) comparing said sample value with a predetermined reference value; and
      if said sample value is higher than said reference value,
   c1) concluding that the subject belongs to the second group; and
      if said sample value is lower than or equal to said reference value,
   c2) concluding that the subject belongs to the first group.

2. Method for determining a prognosis for a mammalian subject having a bladder cancer, comprising the steps of:
   a) evaluating an amount of PODXL in at least part of a sample earlier obtained from the subject and determining a sample value corresponding to the evaluated amount;
   b) comparing said sample value with a reference value associated with a reference prognosis; and
      if said sample value is higher than said reference value,
   c1) concluding that the prognosis for said subject is worse than said reference prognosis; or
      if said sample value is lower than or equal to said reference value,
   c2) concluding that the prognosis for said subject is better than or equal to said reference prognosis.

3. Method according to item 1 or 2, wherein said prognosis is a probability of survival, such as overall survival, progression-free survival or disease-specific survival.

4. Method according to item 3, wherein the probability of survival is a probability of five-year, ten-year or 15-year survival.

5. Method for determining whether a subject having a bladder cancer is not in need of a bladder cancer treatment regimen, comprising the steps of:
   a) evaluating an amount of PODXL in at least part of a sample earlier obtained from the subject and determining a sample value corresponding to the evaluated amount;
   b) comparing said sample value with a predetermined reference value; and
      if said sample value is lower than or equal to said reference value,
   c) concluding that said subject is not in need of the bladder cancer treatment regimen.

6. Non-treatment strategy method for a subject having a bladder cancer, comprising the steps of:
   a) evaluating an amount of PODXL in at least part of a sample earlier obtained from the subject and determining a sample value corresponding to the evaluated amount;
   b) comparing said sample value with a predetermined reference value; and
      if said sample value is lower than or equal to said reference value,
   c) refraining from treating said subject with a bladder cancer treatment regimen.

7. Method of treatment of a subject having a bladder cancer, comprising the steps of:
   a) evaluating an amount of PODXL in at least part of a sample earlier obtained from the subject and determining a sample value corresponding to the evaluated amount;
   b) comparing said sample value with a predetermined reference value; and
      if said sample value is higher than said reference value,
   c) treating said subject with a first treatment regimen; and
      if said sample value is lower than or equal to said reference value,
   d) treating said subject with a second treatment regimen,
   wherein said first treatment regimen is more comprehensive than the second treatment regimen.

8. Method according to any one of the preceding items, wherein the bladder cancer is in stage Ta or T1.

9. Method according to any one of items 1-7, wherein the bladder cancer is invasive.

10. Method according to item 9, wherein the bladder cancer is in stage T2.

11. Method according to any one of the preceding items, wherein the bladder cancer is of grade 1 or 2.

12. Method according to any one of items 1-10, wherein the bladder cancer is of grade 3.

13. Method according to any one of items 1-10, wherein the bladder cancer is of grade 1-2a.

14. Method according to any one of items 1-10, wherein the bladder cancer is of grade 2b-4.

15. Method for determining whether a subject having a stage Ta or T1 bladder cancer is in need of a treatment selected from the group consisting of chemotherapy, *Bacillus* Calmette-Guerin (BCG) treatment and primary cystectomy, comprising the steps of:

a) evaluating an amount of PODXL in at least part of a sample earlier obtained from the subject and determining a sample value corresponding to the evaluated amount;
b) comparing said sample value with a predetermined reference value; and
if said sample value is higher than said reference value,
c) concluding that said subject is in need of the treatment.

16. Method for determining whether a subject having an invasive bladder cancer is in need of a chemotherapy, a biological treatment and/or a radiation therapy, comprising the steps of:
a) evaluating an amount of PODXL in at least part of a sample earlier obtained from the subject and determining a sample value corresponding to the evaluated amount;
b) comparing said sample value with a predetermined reference value; and
if said sample value is higher than said reference value,
c) concluding that said subject is in need of the chemotherapy, the biological treatment and/or the radiation therapy.

17. Method according to item 16, wherein the chemotherapy is adjuvant.

18. Method according to item 16, wherein the chemotherapy is neo-adjuvant.

19. Method according to item 17, wherein the subject has undergone radical cystectomy.

20. Method of treatment of a subject having a stage Ta or T1 bladder cancer, comprising the steps of:
a) evaluating an amount of PODXL in at least part of a sample earlier obtained from the subject and determining a sample value corresponding to the evaluated amount;
b) comparing said sample value with a predetermined reference value; and
if said sample value is higher than said reference value,
c) treating said subject with a treatment selected from the group consisting of chemotherapy, *Bacillus* Calmette-Guerin (BCG) treatment and primary cystectomy.

21. Method of treatment of a subject having an invasive bladder cancer, comprising the steps of:
a) evaluating an amount of PODXL in at least part of a sample earlier obtained from the subject and determining a sample value corresponding to the evaluated amount;
b) comparing said sample value with a predetermined reference value; and
if said sample value is higher than said reference value,
c) applying a chemotherapy, a biological treatment and/or a radiation therapy.

22. Method according to item 21, wherein the chemotherapy is adjuvant.

23. Method according to item 21, wherein the chemotherapy is neo-adjuvant.

24. Method according to item 22, wherein the subject has undergone radical cystectomy.

25. Method according to any one of the preceding items, wherein said sample comprises tumor cells from said subject.

26. Method according to any one of the preceding items, wherein said sample is a bladder tumor tissue sample.

27. Method according to any one of items 1-25, wherein said sample is a urine sample.

28. Method according to any one of the preceding items, wherein the evaluation of step a) is limited to the membranes and/or cytoplasms of tumor cells of the sample.

29. Method according to any one of the preceding items, wherein the evaluation of step a) is limited to the membranes of tumor cells of the sample.

30. Method according to any one of the preceding items, wherein the evaluation of step a) is limited to tumor budding cells of said sample.

31. Method according to any one of the preceding items, wherein the bladder cancer is urothelial cancer.

32. Method according to any one of the preceding items, wherein said subject is a human.

33. Method according to any one of the preceding items, wherein said reference value is a value corresponding to a predetermined amount of PODXL protein in a reference sample.

34. Method according to any preceding item, wherein the sample value of step a) is determined as being either 1, corresponding to detectable membranous PODXL protein expression in tumor cells of the sample, or 0, corresponding to no detectable membranous PODXL protein in tumor cells of the sample.

35. Method according to any preceding item, wherein the reference value of step b) corresponds to a reference sample having no detectable membranous PODXL protein in tumor cells.

36. Method according to any preceding item, wherein the reference value of step b) is 0.

37. Method according to any one of the preceding items, wherein the amino acid sequence of the PODXL protein comprises a sequence selected from
   i) SEQ ID NO:1; and
   ii) a sequence which is at least 85% identical to SEQ ID NO:1.

38. Method according to any one of the preceding items, wherein the amino acid sequence of the PODXL protein comprises or consists of a sequence selected from:
   i) SEQ ID NO:2 or 3; and
   ii) a sequence which is at least 85% identical to SEQ ID NO:2 or 3.

39. Method according to any one of the preceding items, wherein step a) comprises:
   aI) applying to said sample of step a) a quantifiable affinity ligand capable of selective interaction with the PODXL protein to be evaluated, said application being performed under conditions that enable binding of the affinity ligand to PODXL protein present in the sample; and
   aII) quantifying the affinity ligand bound to said sample to evaluate said amount.

40. Method according to any one of items 1-38, wherein step a) comprises:
   a1) applying to said sample or step a) a quantifiable affinity ligand capable of selective interaction with the PODXL protein to be quantified, said application being performed under conditions that enable binding of the affinity ligand to PODXL protein present in the sample;
   a2) removing non-bound affinity ligand; and
   a3) quantifying affinity ligand remaining in association with the sample to evaluate said amount.

41. Method according to item 39 or 40, wherein the quantifiable affinity ligand is selected from the group consisting of antibodies, fragments thereof and derivatives thereof.

42. Method according to item 41, wherein said quantifiable affinity ligand is obtainable by a process comprising a step of immunizing an animal with a peptide whose amino acid sequence consists of the sequence SEQ ID NO:1.

43. Method according to item 39 or 40, wherein said quantifiable affinity ligand is an oligonucleotide molecule.

44. Method according to item 39 or 40, wherein the quantifiable affinity ligand is a protein ligand derived from a scaffold selected from the group consisting of staphylococcal protein A and domains thereof, lipocalins, ankyrin repeat domains, cellulose binding domains, γ crystallines, green fluorescent protein, human cytotoxic T lymphocyte-associated antigen 4, protease inhibitors, PDZ domains, peptide aptamers, staphylococcal nuclease, tendamistats, fibronectin type III domain and zinc fingers.

45. Method according to any one of items 39-44, wherein said quantifiable affinity ligand is capable of selective interaction with a peptide whose amino acid sequence consists of the sequence SEQ ID NO:1.

46. Method according to any one of items 39-45, wherein said quantifiable affinity ligand is capable of selective interaction with a peptide whose amino acid sequence consists of the sequence SEQ ID NO:8, 13 or 14.

47. Method according to any one of items 39-46, wherein the quantifiable affinity ligand comprises a label selected from the group consisting of fluorescent dyes and metals, chromophoric dyes, chemiluminescent compounds and bioluminescent proteins, enzymes, radioisotopes, particles and quantum dots.

48. Method according to any one of items 39-47, in which said quantifiable affinity ligand is detected using a secondary affinity ligand capable of recognizing the quantifiable affinity ligand.

49. Method according to item 48, in which said secondary affinity ligand capable of recognizing the quantifiable affinity ligand comprises a label selected from the group consisting of fluorescent dyes and metals, chromophoric dyes, chemiluminescent compounds and bioluminescent proteins, enzymes, radioisotopes, particles and quantum dots.

50. Use ex vivo of a PODXL protein as a prognostic marker for bladder cancer.

51. Use according to item 50, wherein said protein is provided in a sample from a subject having a bladder cancer.

52. Use according to item 51, wherein said sample is a bladder cancer tissue sample.

53. Use according to any one of items 50-52, wherein said marker is a marker of a relatively poor prognosis for bladder cancer.

54. Use ex vivo of an PODXL protein, or an antigenically active fragment thereof, for the selection or purification of a bladder cancer prognostic agent.

55. Use of an PODXL protein, or an antigenically active fragment thereof, for the production of a bladder cancer prognostic agent.

56. Use according to item 54 or 55, wherein said prognostic agent is an affinity ligand capable of selective interaction with the PODXL protein or the antigenically active fragment thereof.

57. Use according any one of items 50-56, wherein the amino acid sequence of the PODXL protein comprises a sequence selected from:
 i) SEQ ID NO: 1; and
 ii) a sequence which is at least 85% identical to SEQ ID NO: 1.

58. Use according any one of items 50-56, wherein the amino acid sequence of the PODXL protein comprises or consists of a sequence selected from:
 i) SEQ ID NO: 2 or 3; and
 ii) a sequence which is at least 85% identical to SEQ ID NO:2 or 3.

59. Use of an antigenically active fragment according to any one of items 54-56, wherein the fragment consists of 50 amino acid residues or less and comprises the amino acid sequence SEQ ID NO:8, 13 or 14.

60. Use according to item 59, wherein the fragment consists of 25 amino acid residues or less, such as 20 amino acids or less.

61. Use ex vivo of an affinity ligand capable of selective interaction with a PODXL protein as a bladder cancer prognostic agent.

62. Use according to item 61, wherein the affinity ligand is obtainable by a process comprising a step of immunizing an animal with a peptide whose amino acid sequence consists of sequence SEQ ID NO: 1.

63. Use according to item 61, wherein the affinity ligand is obtainable by a process comprising a step of immunizing an animal with a peptide whose amino acid sequence consists of SEQ ID NO:8, 13 or 14.

64. Use according to item 61, wherein the affinity ligand is capable of selective interaction with a peptide consisting of the amino acid sequence SEQ ID NO: 1.

65. Use according to item 61, wherein the affinity ligand is capable of selective interaction with a peptide consisting of the amino acid sequence SEQ ID NO:8, 13 or 14.

66. Use according to anyone of items 61-65, wherein the affinity ligand is selected from the group consisting of antibodies, fragments thereof and derivatives thereof.

67. Use according to item 66, wherein the antibody fragments are selected from the group consisting of Fab fragments, Fv fragments and single chain Fv fragments (scFv).

68. Use according to item 66, wherein the antibodies are monoclonal or polyclonal antibodies.

BRIEF DESCRIPTION OF THE FIGURES

FIG. 2 shows the impact of PODXL expression on overall survival (OS) of patients in cohort I. Patients were divided into two groups based on PODXL expression. The solid line represents patients with tumors without membranous PODXL expression, and the dotted line represents patients with tumors expressing membranous PODXL.

FIG. 3 shows the impact of PODXL expression on overall survival (OS) of patients in cohort I. Patients were divided into two groups based on PODXL expression. The solid line represents patients with tumors without membranous PODXL expression, and the dotted line represents patients with tumors expressing membranous PODXL.

FIG. 5 shows the impact of PODXL expression on 5-year overall survival (OS) of patients in cohort II. Patients were divided into two groups based on PODXL expression. The solid line represents patients with tumors without membranous PODXL expression, and the dotted line represents patients with tumors expressing membranous PODXL.

FIG. 7 shows the impact of PODXL expression on disease specific survival (DSS) of patients in cohort II. Patients were divided into two groups based on PODXL expression. The solid line represents patients with tumors without membranous PODXL expression, and the dotted line represents patients with tumors expressing membranous PODXL.

DETAILED DESCRIPTION

Figure 1:
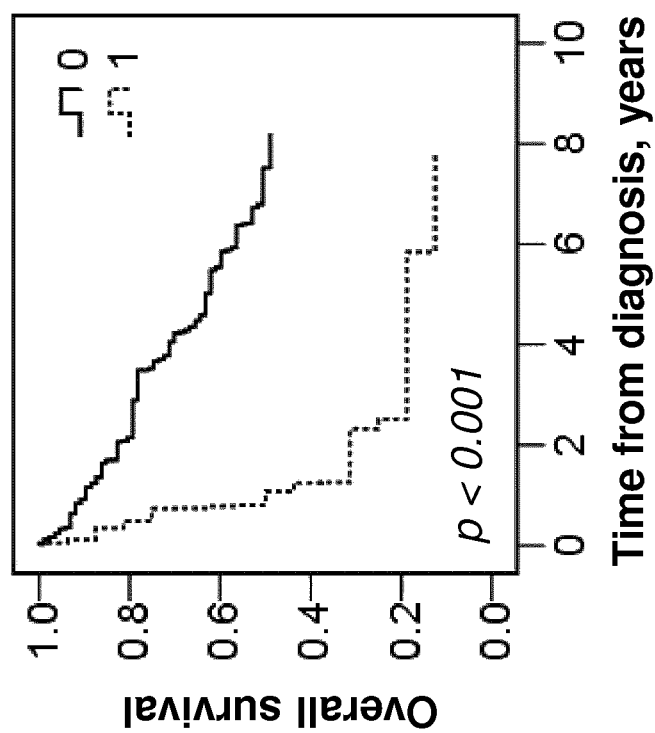
FIG. 1 shows the impact of membranous PODXL expression on overall survival (OS) of all patients in cohort I, i.e. 103 subjects, diagnosed with urothelial cancer. Patients were divided into two groups based on PODXL expression. The solid line represents patients with tumors without membranous PODXL expression, and the dotted line represents patients with tumors expressing membranous PODXL.

As a first aspect of the present disclosure, there is thus provided a method for determining whether a mammalian subject having a bladder cancer belongs to a first or a second group, wherein the prognosis of subjects of the second group is worse than the prognosis of subjects of the first group, comprising the steps of:
- a) evaluating an amount of PODXL in at least part of a sample earlier obtained from the subject and determining a sample value corresponding to the evaluated amount;
- b) comparing said sample value with a predetermined reference value; and
    if said sample value is higher than said reference value,
- c1) concluding that the subject belongs to the second group; and
    if said sample value is lower than or equal to said reference value,
- c2) concluding that the subject belongs to the first group.

The present invention, based on a PODXL level as a bladder cancer status indicator, has a number of benefits. As well known by the person skilled in the art, a prognosis may be important for various reasons. Frequently, the prognosis for a bladder cancer subject reflects the aggressiveness of the cancer. In general, identification of the level of aggressiveness of a bladder cancer is of vital importance as it helps a physician selecting an appropriate treatment strategy. The level of PODXL expression may for example be used for identifying particularly aggressive forms of the cancer. In such cases, a more comprehensive treatment than what is normally considered may be applied. For example, the subject may be given a painful or in any other sense unpleasant treatment, which normally is avoided, when the PODXL level indicates that the cancer is aggressive.

Also, in case of a subject having a bladder cancer of an advanced stage, the additional prognostic information provided by the methods of the present disclosure may guide the physician (and the subject) deciding whether to apply an aggressive treatment in hope of prolonged survival or proceed with palliative treatment to relieve the subject from suffering during the remaining time. A low PODXL level (e.g. absent membranous expression) would here be in favor of the former alternative and a high PODXL and a high PODXL level (e.g. membranous expression) would be in favor of the latter alternative.

In addition, the PODXL protein, as a marker for which a certain level of expression is correlated with a certain pattern of disease progression, has a great potential for example in a panel for making predictions or prognoses or for the selection of a treatment regimen.

In the method of the first aspect, it is determined whether a bladder cancer subject belongs to a first or a second group, wherein subjects of the second group generally have a worse prognosis than subjects of the first group. The division of bladder cancer subjects into the two groups is determined by comparing samples values from the subjects with a reference value. Various reference values may be employed to discriminate between subjects that generally survived for a comparatively long period and subjects that generally survived for a comparatively short period. The reference value is thus the determinant for the size of the respective groups; the higher the reference value, the fewer the subjects in the second group and the lower the likelihood that a tested subject belongs to the second group. As the prognosis generally worsens when the sample value increases, a relatively high reference value may in some instances be selected to identify subjects with a particularly poor prognosis. Guided by the present disclosure, the person skilled in the art may select relevant reference values without undue burden.

The first and the second group may consist exclusively of subjects having bladder cancers of the same or similar grade, stage and/or type as the tested subject.

When the first and the second group consist exclusively of subjects having bladder cancers of the same stage as the tested subject, the prognosis is a stage-independent prognosis. A stage-independent prognosis is particularly interesting as it provides information beyond what is available from the traditional staging.

When the first and the second group consist exclusively of subjects having bladder cancers of the same grade as the tested subject, the prognosis is a grade-independent prognosis. A grade-independent prognosis is particularly interesting as it provides information beyond what is available from the traditional grading.

Further, the groups may consist only of subjects having the same or similar age, race, sex, genetic characteristics and/or medical status or history.

Consequently, a physician may use the method according to the first aspect to obtain additional information regarding the prognosis of a bladder cancer subject, which in turn may help him to make informed decisions regarding following actions.

The prognosis of the tested subject may also be determined relative to a reference prognosis. Accordingly, as a first configuration of the first aspect, there is provided a method for determining a prognosis for a mammalian subject having a bladder cancer, comprising the steps of:
- c) evaluating an amount of PODXL in at least part of a sample earlier obtained from the subject and determining a sample value corresponding to the evaluated amount;
- d) comparing said sample value with a reference value associated with a reference prognosis; and
    if said sample value is higher than said reference value,
- c1) concluding that the prognosis for said subject is worse than said reference prognosis; or
    if said sample value is lower than or equal to said reference value, c2) concluding that the prognosis for said subject is better than or equal to said reference prognosis.

However closely related and covered by the same concept, c1) and c2) provide two alternative conclusions.

Similarly and as a second configuration of the first aspect, there is provided a method for determining whether a prognosis for a mammalian subject having a bladder cancer is worse than or equal to a reference prognosis, comprising the steps of:
a) evaluating an amount of PODXL in at least part of a sample earlier obtained from the subject and determining a sample value corresponding to the evaluated amount;
b) comparing said sample value with a reference value associated with a reference prognosis; and
   if said sample value is higher than said reference value,
c1) concluding that the prognosis for said subject is worse than said reference prognosis.

The inventive concept of the present disclosure may also form the basis for a decision to refrain from a certain treatment regimen.

For example, the prognoses for subjects showing low PODXL levels are generally better than those for subjects showing high PODXL levels, as shown in the attached figures. Provided with the teachings of the present disclosure, a physician may conclude that a more aggressive treatment regimen is not motivated and that a less aggressive treatment regimen is sufficient when the PODXL level is low. In case of a non-invasive cancer (Ta or T1), the physician may thus refrain from chemotherapy, Bacillus Calmette-Guerin (BCG) treatment and/or primary cystectomy if it is found that a relevant tumor tissue sample lacks membranous PODXL expression. Further, the physician may refrain from chemotherapy and/or radiation therapy if it is found that a relevant tumor tissue sample lacks membranous PODXL expression in case of invasive cancer.

Thus, as a third configuration of the first aspect, there is provided a method for determining whether a subject having a bladder cancer is not in need of a bladder cancer treatment regimen, comprising the steps of:
a) evaluating an amount of PODXL in at least part of a sample earlier obtained from the subject and determining a sample value corresponding to the evaluated amount;
b) comparing said sample value with a predetermined reference value; and
   if said sample value is lower than or equal to said reference value,
c) concluding that said subject is not in need of the bladder cancer treatment regimen.

Further, as a fourth configuration of the first aspect, there is provided a non-treatment strategy method for a subject having a bladder cancer, comprising the steps of:
a) evaluating an amount of PODXL in at least part of a sample earlier obtained from the subject and determining a sample value corresponding to the evaluated amount;
b) comparing said sample value with a predetermined reference value; and
   if said sample value is lower than or equal to said reference value,
c) refraining from treating said subject with a bladder cancer treatment regimen For example, step c) of the fourth configuration may be a refraining from the treatment regimen during at least one week from the completion of steps a)-b), such as at least one month from the completion of steps a)-b), such as at least three months from the completion of steps a)-b), such as at least six months from the completion of steps a)-b), such as at least one year from the completion of steps a)-b), such as at least two years from the completion of steps a)-b).

Alternatively, the refraining of step c) may be a refraining from treatment until the next time the method is performed or until a recurrence of a bladder cancer.

The treatment regimen of the present disclosure may comprise or consist of surgery, such as radical cystectomy. Further, the treatment regimen of the present disclosure may be an adjuvant and/or a neo-adjuvant therapy. Such a treatment regimen may for example comprise or consist of chemotherapy and/or administration of Bacillus Calmette-Guérin (BCG).

Further, the treatment regimen may comprise biological therapy, such as application of interleukin 2, sorafenib, sunitinib or lapatinib. The biological treatment may be combined with chemotherapy The treatment regimen may also comprise or consist of radiation therapy. Chemotherapy and/or biological therapy may be carried out before or after radiation therapy.

As an alternative configuration of the first aspect, there is provided a method for establishing a prognosis for a mammalian subject having a bladder cancer, comprising the steps of:
a) evaluating an amount of PODXL protein present in at least part of a sample from the subject, and determining a sample value corresponding to the evaluated amount; and
b) correlating the sample value of step a) to the prognosis for the subject.

In an embodiment of the alternative configuration, the sample may be an earlier obtained sample.

The correlating of step b) of the alternative configuration refers to any way of associating survival data to the obtained sample value so as to establish a prognosis for the subject.

In the context of the present disclosure, "establishing a prognosis" refers to establishing a specific prognosis or a prognosis interval.

In the present disclosure, different PODXL values (sample values) corresponding to various prognoses are presented. Typically, a high sample value is associated with a worse prognosis than a low sample value.

The "reference prognosis" of the configurations of the first aspect may be based on a previously established prognosis, e.g., obtained by an examination of a relevant population of subjects. Such reference population may be selected to match the tested subject's age, sex, race, bladder cancer stage, grade and/or type and/or medical status and history. Further, a prognosis may be adapted to a background risk in the general population, a statistical prognosis/risk or an assumption based on an examination of the subject. Such examination may also comprise the subject's age, sex, race, bladder cancer stage, bladder cancer type and/or medical status and history. Thus, a physician may for example adapt the reference prognosis to the subject's bladder cancer history, the type, grade and/or stage of the tumor, the morphology of the tumor, the location of the tumor, the presence and spread of metastases and/or further cancer characteristics.

In general, when deciding on a suitable treatment strategy for a patient having bladder cancer, the physician responsible for the treatment may take several parameters into account, such as the result of an immunohistochemical evaluation, patient age, tumor type, stage and grade, general condition and medical history, such as bladder cancer history. To be guided in the decision, the physician may perform a PODXL test, or order a PODXL test performed, according to the first aspect. Further, the physician may assign to someone else, such as a lab worker, to perform step a), and optionally step b), while performing step c), and optionally b), himself.

The inventive concept of the present disclosure may also form the basis for applying various treatment regimens.

For example, the prognosis for subjects showing high PODXL levels is generally worse than those for subjects showing low PODXL protein levels, as shown in the attached figures. Accordingly, a physician may consider the prognosis of a PODXL protein high subject as being so poor that a certain treatment regimen is appropriate. The present disclosure may thus provide for accurate treatment of a previously undertreated group.

As a first configuration of a second aspect of the present disclosure, there is provided a method of treatment of a subject having a bladder cancer, comprising the steps of:
  a) evaluating an amount of PODXL in at least part of a sample earlier obtained from the subject and determining a sample value corresponding to the evaluated amount;
  b) comparing said sample value with a predetermined reference value; and
    if said sample value is higher than said reference value,
  c) treating said subject with a first treatment regimen; and
    if said sample value is lower than or equal to said reference value,
  d) treating said subject with a second treatment regimen, wherein said first treatment regimen is more comprehensive than the second treatment regimen.

The skilled person understands when one treatment regimen is more comprehensive than another treatment. For example, the first treatment may be a combination of two or more from the group consisting of TUR-B, BCG, cystectomy, chemotherapy and radiation therapy, while the second treatment is only one from the same group, such as only TUR-B. In another example, which is particularly relevant for cancer in situ, the first treatment is intravesical instillation during a first period, while the second treatment is intravesical instillation during a second period, which is shorter than the first period. The intravesical instillation is normally a BCG treatment. In yet another example, the first treatment is cystectomy and neo-adjuvant or adjuvant treatment, while the second only cystectomy.

In the group of subjects having non-invasive bladder cancer, it is of particular importance to identify the subjects that should be given a more aggressive first-line treatment or primary cystectomy, even though their tumors are of early stage. As a second configuration of the second aspect of the present disclosure, there is thus provided a method of treatment of a subject having a stage Ta or T1 bladder cancer, comprising the steps of:
  a) evaluating an amount of PODXL in at least part of a sample earlier obtained from the subject and determining a sample value corresponding to the evaluated amount;
  b) comparing said sample value with a predetermined reference value; and
    if said sample value is higher than said reference value,
  c) treating said subject with a treatment selected from the group consisting of chemotherapy, *Bacillus* Calmette-Guerin (BCG) treatment and primary cystectomy.

The treatment of step c) may comprise two or more of the treatments in the group.

According to one embodiment of the second configuration of the second aspect, the method may comprise the additional step:
  d) and if said sample value is lower than or equal to said reference value, refraining from treating said subject with the treatment.

When the cancer is in stage Ta, the treatment is preferably chemotherapy or BCG. In such case, the TUR-B may be the only treatment when the PODXL level is low (e.g. absent in the membranes of tumor cells).

When the cancer is in stage T1, the treatment is preferably cystectomy, possibly in combination chemotherapy or BCG.

In the group of subjects having invasive bladder cancer, it is of particular importance to identify the subjects that, in addition to the cystectomy that is normally performed, should be given neo-adjuvant or adjuvant treatment. As a third configuration of the second aspect of the present disclosure, there is thus provided a method of treatment of a subject having an invasive bladder cancer, comprising the steps of:
  a) evaluating an amount of PODXL in at least part of a sample earlier obtained from the subject and determining a sample value corresponding to the evaluated amount;
  b) comparing said sample value with a predetermined reference value; and
    if said sample value is higher than said reference value,
  c) applying a treatment selected from the group consisting of chemotherapy, biological treatment and radiation therapy.

In one embodiment, the treatment of step c) is chemotherapy.

The treatment of step c) may in another embodiment comprise both chemotherapy and radiation therapy.

According to one embodiment of the third configuration of the second aspect, the method may comprise the additional step:
  e) and if said sample value is lower than or equal to said reference value, refraining from treating said subject with the treatment.

As mentioned above, the subjects of the third configuration of the second aspect normally undergo radical cystectomy either before or after the chemotherapy or radiation therapy. The chemotherapy and/or radiation therapy of step c) may thus be adjuvant or neo-adjuvant.

The physician responsible for the treatment according to the second aspect may assign to someone else, such as a lab worker, to perform step a), and optionally step b), while performing step c), and optionally b), himself.

Further, the results of steps a) and b) may be at hand when the method of treatment according to the second aspect is initiated.

The method of treatment may also be limited to the decision-making and treatment. Thus, as a fourth configuration of the second aspect, there is provided a method of treatment of a subject having a bladder cancer, comprising:
  α) comparing a sample value corresponding to a level of PODXL in a sample from the subject with a reference value; and,
    if said sample value is higher than said reference value,
  β) treating said subject with a bladder cancer treatment regimen.

Numerous ways of obtaining a sample value corresponding to a level of PODXL in a sample from a subject are described in the present disclosure. The bladder cancer treatment regimen of β) may be selected according to the above.

Further, the skilled person should recognize that the usefulness of the methods according to the above aspects is not limited to the quantification of any particular variant of the PODXL protein present in the subject in question, as long as the protein is encoded by the relevant gene and presents the relevant pattern of expression. As a non-limiting example, the PODXL protein may comprise a sequence selected from:
  i) SEQ ID NO:1; and
  ii) a sequence which is at least 85% identical to SEQ ID NO:1.

In some embodiments, sequence ii) above is at least 90% identical, at least 91% identical, at least 92% identical, at least 93% identical, at least 94% identical, at least 95% identical, at least 96% identical, at least 97 identical, at least 98% identical or at least 99% identical to SEQ ID NO:1.

As another non-limiting example, the PODXL protein may comprise, or consists of, a sequence selected from:
  i) SEQ ID NO:2 or 3; and
  ii) a sequence which is at least 85% identical to SEQ ID NO:2.

SEQ ID NO:2 and 3 are two splice variants of the PODXL protein. SEQ ID NO:1 is a subregion which is common to the extracellular regions of the respective splice variants.

In some embodiments, sequence ii) above is at least 90% identical, at least 91% identical, at least 92% identical, at least 93% identical, at least 94% identical, at least 95% identical, at least 96% identical, at least 97 identical, at least 98% identical or at least 99% identical to SEQ ID NO:2 or 3.

The term "% identical", as used in the context of the present disclosure, is calculated as follows. The query sequence is aligned to the target sequence using the CLUSTAL W algorithm (Thompson, J. D., Higgins, D. G. and Gibson, T. J., Nucleic Acids Research, 22: 4673-4680 (1994)). The amino acid residues at each position are compared, and the percentage of positions in the query sequence that have identical correspondences in the target sequence is reported as % identical. Also, the target sequence determines the number of positions that are compared. Consequently, in the context of the present disclosure, a query sequence that is shorter than the target sequence can never be 100% identical to the target sequence. For example, a query sequence of 85 amino acids may at the most be 85% identical to a target sequence of 100 amino acids.

Regarding step a) of the methods of the present disclosure, an increase in the amount of PODXL typically results in an increase in the sample value, and not the other way around. However, in some embodiments, the evaluated amount may correspond to any of a predetermined number of discrete sample values. In such embodiments, a first amount and a second, increased, amount may correspond to the same sample value. In any case, an increase in the amount of PODXL protein will not result in a decrease in the sample value in the context of the present disclosure.

However inconvenient, but in an equivalent fashion, the evaluated amounts may be inversely related to sample values if the qualification between step b) and c) is inverted. For example, the qualification between step b) and c) is inverted if the phrase "if the sample value is higher than the reference value" is replaced with "if the sample value is lower than the reference value".

In the context of the present disclosure, "prognosis" refers to the prediction of the course or outcome of a disease and its treatment. For example, prognosis may also refer to a determination of chance of survival or recovery from a disease, as well as to a prediction of the expected survival time of a subject. A prognosis may specifically involve establishing the likelihood for survival of a subject during a period of time into the future, such as three years, five years, ten years or any other period of time. A prognosis may further be represented by a single value or a range of values.

Further, in the context of the methods of the present disclosure, "earlier obtained" refers to obtained before the method is performed. Consequently, if a sample earlier obtained from a subject is used in a method, the method does not involve obtaining the sample from the subject, i.e., the sample was previously obtained from the subject in a step separate from the method.

The methods and uses of the present disclosure, except the methods of treatment, may unless otherwise stated or indicated be carried out entirely ex vivo.

Further, in the context of the present disclosure, "a mammalian subject having a bladder cancer" refers to a mammalian subject having a primary bladder tumor or a mammalian subject which has had a primary bladder tumor removed, wherein the removal of the tumor refers to eradicating the tumor by any appropriate type of surgery or therapy. In the method and use aspects of the present disclosure, "a mammalian subject having a bladder cancer" also includes the cases wherein the mammalian subject is suspected of having a bladder cancer at the time of the use or the performance of the method and the bladder cancer diagnosis is established later.

Further, in the context of the present disclosure, the "predetermined reference value" refers to a predetermined value found to be relevant for making decisions or drawing conclusions regarding the prognosis or a suitable treatment strategy for the subject.

Also, in the context of the present disclosure, a reference value being "associated" with a reference prognosis refers to the reference value being assigned a corresponding reference prognosis, based on empirical data and/or clinically relevant assumptions. For example, the reference value may be the average PODXL value in a relevant group of subjects and the reference prognosis may be an average survival in the same group. Further, the reference value does not have to be assigned to a reference prognosis directly derived from prognosis data of a group of subjects exhibiting the reference value. The reference prognosis may for example correspond to the prognosis for subjects exhibiting the reference value or lower. That is, if the reference value is 1 on a scale from 0 to 2, the reference prognosis may be the prognosis of the subjects exhibiting the values 0 or 1. Consequently, the reference prognosis may also be adapted to the nature of the available data. As further discussed above, the reference prognosis may be further adapted to other parameters as well.

Step a) of the methods of the above aspects involve evaluating an amount of PODXL present in at least part of the sample, and determining a sample value corresponding to the amount. The "at least part of the sample" refers to a relevant part or relevant parts of the sample for establishing the prognosis or drawing conclusions regarding suitable treatments. The person skilled in the art understands which part or parts that are relevant under the circumstances present when performing the method. For example, if evaluating a sample comprising cells, the skilled person may only consider the tumor cells, or only the nuclei of tumor cells, of the sample.

Further, in step a) an amount is evaluated and a sample value corresponding to the amount is determined. Consequently, an exact measurement of the amount of PODXL is not required for obtaining the sample value. For example, the amount of PODXL may be evaluated by visual inspection of a prepared and stained tissue sample and the sample value may then be categorized as for example high or low based on the evaluated amount.

The chemotherapy of the present disclosure may for example be application of epirubicin, gemcitabine and/or mitomycin. Other examples of chemotherapies are platinum-based treatments, such as application of carboplatin, paraplatin, oxaliplatin, satraplatin, picoplatin or cisplatin. Still other examples of chemotherapeutic agents that may be applied are docetaxel, methotrexate, vinblastine, doxorubicin, mitomycin C, thiotepa, valrubicin, and vinflunine.

Cisplatin may for example be applied in combination with methotrexate, vinblastine and/or doxorubicin. A combination of all of these agents (sometimes referred to as MVAC) may be applied in cases of advanced disease (of poor prognosis), even though normally associated with severe side-effects. Cisplatin may also be applied in combination with gemcitabine. Gemcitabine may also be applied in combination with carboplatin, in particular when the subject is intolerant of cisplatin.

Figure 6:
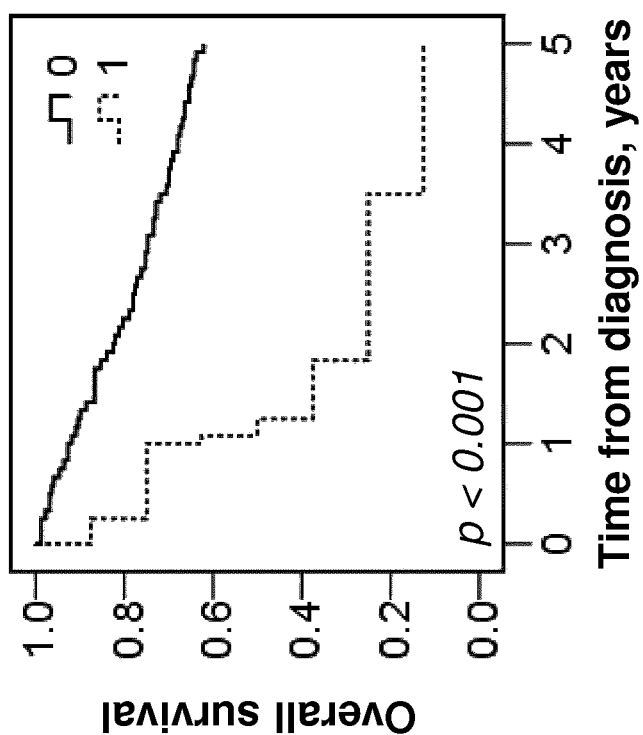
FIG. 6 shows the impact of membranous PODXL expression on 5-year overall survival (OS) of patients in cohort II diagnosed with stage Ta or T1 urothelial cancer, i.e. 230 subjects. Patients were divided into two groups based on PODXL expression. The solid line represents patients with tumors without membranous PODXL expression, and the dotted line represents patients with tumors expressing membranous PODXL.

If a subject is diagnosed with early stage bladder cancer, it may be difficult for the physician responsible for the treatment to decide whether to apply cystectomy or not. As seen in FIG. 6, a group of early stage bladder cancer subjects having a relatively poor prognosis may be identified with a method according to the present disclosure. Subjects having such a poor prognosis may be considered eligible for cystectomy even though their cancer is of an early stage. In other words, the inventive methods may be particularly relevant for a subject having an early stage bladder cancer, such as a cancer of TNM stage Ta or T1.

Further, it may be difficult for a physician to decide whether to apply chemotherapy or not to a subject having an invasive bladder cancer, such as a stage T2 bladder cancer. In such a case, a high PODXL value may advise the physician to apply the chemotherapy while a low PODXL value may advise may the physician to refrain from such a treatment. Thus, an PODXL high T2N0 bladder cancer subject may be given neoadjuvant chemotherapy even though subjects having cancers of that stage are normally not given such treatment. Thus, in some embodiments of the present disclosure, the bladder cancer is of stage T2 (see also FIG. 3B).

Figure 5B:
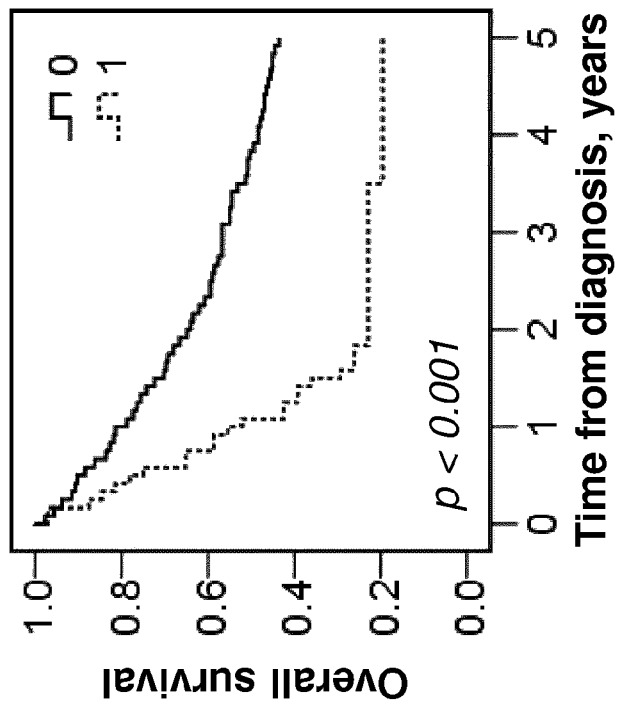
FIG. 5B shows patients diagnosed with high grade (2B-4) urothelial cancer, i.e. 261 subjects.
Figure 5A:
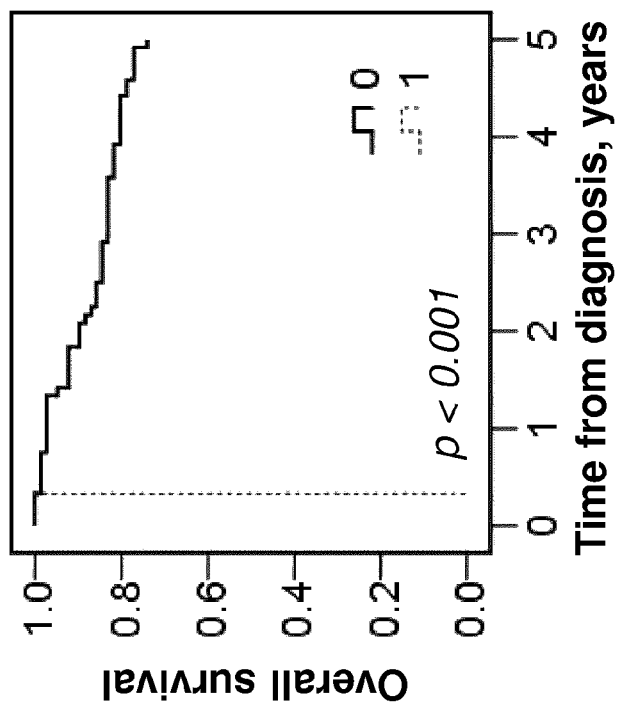
FIG. 5A shows patients diagnosed with low grade (1-2A) urothelial cancer, i.e. 82 subjects.

The prognostic relevance of the level of PODXL is particularly accentuated in bladder cancers of lower grade, such as grade 1-2 (see FIG. 2A) or grade 1-2a (see FIG. 5A). However, the level of PODXL is also significantly associated with survival in cancers of higher grade, such as grade 3 (see FIG. 2B) or grade 2B-3 (see FIG. 5B).

Figure 7B:
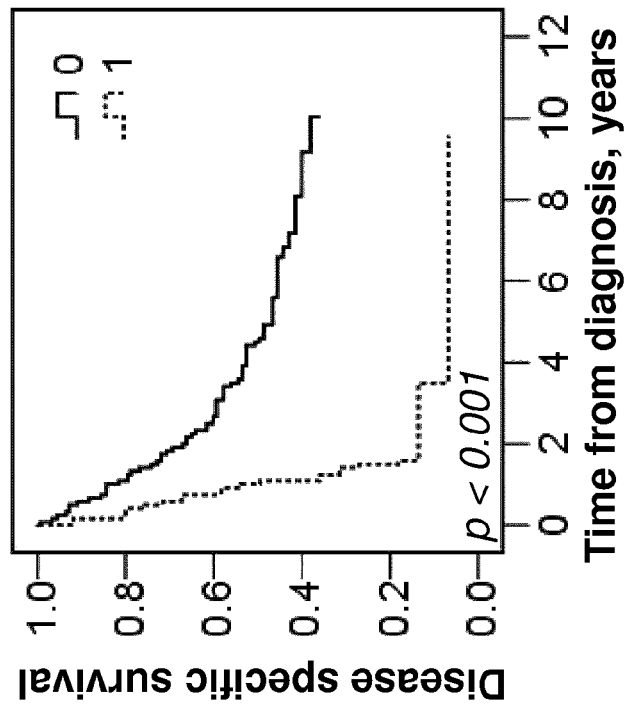
FIG. 7B shows disease free survival.
Figure 7A:
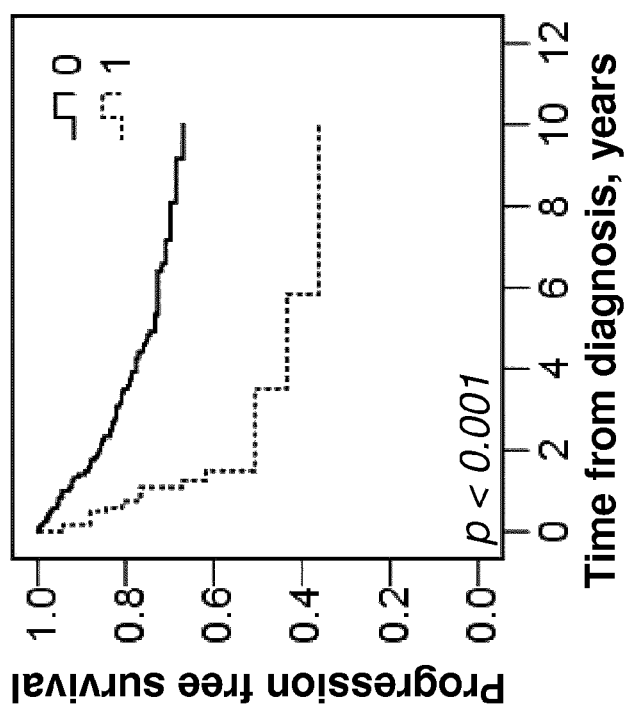
FIG. 7A shows recurrence free survival.

In embodiments of the present disclosure, the prognosis may be a probability of survival, and there are several ways to measure "survival". The survival of the present disclosure may for example be overall survival (see FIGS. 1-6), progression free survival (see FIG. 7A) or disease specific survival (see FIG. 7B). It may also be a recurrence free survival. Further, the "survival" may be measured over different periods, such as five, ten or 15 years. Accordingly, the survival may be a five-year, ten-year or 15-year survival. The skilled person understands that when a reference prognosis is employed, it is of the same type as the prognosis for the subject.

In embodiments of the methods of the above aspects, the sample may be a body fluid sample. For example, the body fluid sample may be selected from the group consisting of blood, plasma, serum, cerebral fluid, urine, lymph, seminal fluid and exudate. Alternatively, the sample may be a cytology sample or a stool sample.

The level of PODXL protein is preferably measured in cells. Thus, the body fluid, cytology or stool sample may for example comprise cells, such as tumor cells.

In further embodiments of the methods of the above aspects, the sample may be a tissue sample, such as a bladder tissue sample, such as a bladder tumor tissue sample, e.g., from a biopsy or a specimen removed with surgery or TUR-B. Thus, the sample may be obtained and the inventive method carried out after transurethral resection of the bladder.

The inventors have noted that the PODXL expression in a subset of tumor cells at the invasive tumor front may be particularly relevant for the establishment of a prognosis or selection of a treatment. Sometimes, such a subset of tumor cells is referred to as "tumor budding cells", see e.g. Prall and Hase et al. (Prall F: Tumour budding in colorectal carcinoma. *Histopathology* 2007, 50(1):151-162 and Hase K et al: Prognostic value of tumor "budding" in patients with colorectal cancer. *Dis Colon Rectum* 1993, 36(7):627-635). The evaluation of step a) may thus be limited to tumor budding cells of said sample.

Further, the inventors have noted that membranous or cytoplasmic, in particular membranous, expression of PODXL protein is relevant for determining prognoses or selecting treatments. The evaluation of step a) may thus be limited to the cytoplasms and/or membranes of cells, such as tumor cells, of said sample.

Consequently, when a tissue sample is examined, only the membranes of tumor cells, such as tumor budding cells, may be taken into consideration. Such examination may for example be aided by immunohistochemical staining.

The tissue samples in the Examples below are from male and female humans, and the inventors have found that the prognostic relevance of PODXL protein is independent of the subject's sex. Accordingly, the subject of the methods of the above aspects may be a human, and further, the subject of the methods of the above aspects may be male or female.

When performing the methods according to the above aspects, it may be convenient to use zero as the reference value, because in such case, it has only to be established in step a) whether PODXL protein is present in the sample or not. The figures show that a value of zero is a working cut-off value for establishing two subgroups of significantly different prognoses when only membranous expression is taken into account.

Thus, in embodiments of the methods of the above aspects, the sample value of step a) may be either 1, corresponding to detectable PODXL protein in the membranes of tumor cells in the sample, or 0, corresponding to no detectable PODXL protein in the membranes of tumor cells of the sample. Consequently, in such embodiments, the evaluation of the sample is digital: PODXL protein is considered to be either present or not. In the context of the present disclosure, "no detectable PODXL protein" refers to an amount of PODXL protein that is so small that it is not, during normal operational circumstances, detectable by a person or an apparatus performing the step a). The "normal operational circumstances" refer to the laboratory methods and techniques a person skilled in the art would find appropriate for performing the methods of the present disclosure.

A sample value of PODXL protein being higher than the reference value, or a subject from which such sample value is obtained, is sometimes referred to herein as being "PODXL protein high". Further, a sample value of PODXL protein being lower than, or equal to, the reference value, or a subject from which such sample value is obtained, is sometimes referred to herein as being "PODXL protein low".

In the context of the present disclosure, the terms "sample value" and "reference value" are to be interpreted broadly. The quantification of PODXL to obtain these values may be done via automatic means, via a scoring system based on visual or microscopic inspection of samples, or via combinations thereof. However, it is also possible for a skilled person, such as a person skilled in the art of histopathology, to determine the sample and/or reference value by inspection, e.g., of tissue slides that have been prepared and stained for PODXL protein expression.

Determining that the sample value is higher than the reference value may thus be determining, upon visual or microscopic inspection, that a sample tissue slide is more densely stained and/or exhibit a larger fraction of stained cells than a reference tissue slide. The sample value may also be compared to a reference value given by a literal reference, such as a reference value described in wording or by a reference picture. Consequently, the sample and/or reference values may in some cases be mental values that the skilled person envisages upon inspection and comparison.

For example, the skilled person may categorize a sample as being PODXL protein high or low, wherein the sample is categorized as high if it contains more PODXL protein than a previously inspected reference sample and low if it contains less or equally much. Such evaluation may be assisted by staining the sample, and, if necessary, a reference sample, with a staining solution comprising e.g., antibodies selective for PODXL protein.

One or more of the steps of the methods of the present disclosure may be implemented in an apparatus. For example, step a) and optionally step b) may be performed in an automatic analysis apparatus, and such an apparatus may be based on a platform adapted for immunohistochemical analysis. As an example, one or more tumor tissue sample(s) from the subject in question may be prepared for imunohistochemical analysis manually and then loaded into the automatic analysis apparatus, which gives the sample value of step a) and optionally also performs the comparison with the reference value of step b). The operator performing the analysis, the physician ordering the analysis or the apparatus itself may then draw the conclusion of step c). Consequently, software adapted for drawing the conclusion of step c) may be implemented on the apparatus.

A reference value, which is relevant for establishing a prognosis or making a treatment decision regarding bladder cancer subjects, for use as comparison with the sample value from the subject, may be provided in various ways. With the knowledge of the teachings of the present disclosure, the skilled artisan can, without undue burden, provide relevant reference values for performing the methods of the present disclosure.

The person performing the methods of the above aspects may, for example, adapt the reference value to desired information. For example, the reference value may be adapted to yield the most significant prognostic information, e.g., the largest separation between the PODXL protein high survival curve and the PODXL protein low survival curve (see the figures), which corresponds to the largest difference in survival between the first and the second group of the first aspect. Alternatively, the reference value may be selected such that a group of subjects having particularly poor prognoses is singled out.

In embodiments of the methods of the above aspects, the reference value may correspond to the amount of PODXL protein expression in a healthy tissue, such as healthy bladder tissue, or stroma tissue of the subject of the method. As another example, the reference value may be provided by the amount of PODXL protein expression measured in a standard sample of normal tissue from another, comparable subject. As another example, the reference value may be provided by the amount of PODXL protein expression measured in a reference sample comprising tumor cells, such as a reference sample of tumor tissue, e.g., bladder tumor tissue. The amount of protein expression of the reference sample may preferably be previously established.

Further, the reference value may for example be provided by the amount of PODXL protein expression measured in a reference sample comprising cell lines, such as cancer cell lines, expressing a predetermined, or controlled, amount of PODXL protein. The person skilled in the art understands how to provide such cell lines, for example guided by the disclosure of Rhodes et al. (2006) The biomedical scientist, p 515-520.

Consequently, the reference value may be provided by the amount of PODXL protein measured in a reference sample comprising cells expressing a predetermined amount of PODXL protein. Accordingly, in embodiments of the methods of the present disclosure, the reference value may be a predetermined value corresponding to the amount of PODXL protein expression in a reference sample.

However, the amount of PODXL protein in the reference sample does not have to directly correspond to the reference value (this is further discussed below). The reference sample may also provide an amount of PODXL protein that helps a person performing the method to assess various reference values. The reference sample(s) may thus help in creating a mental image of the reference value by providing a "positive" reference value and/or a "negative" reference value. For example, there may be provided one reference sample having a positive PODXL expression in the membranes of the tumor cells (a positive reference) and another reference sample having absent PODXL expression in the tumor cells (a negative reference). Here, the latter reference sample may also provide the actual reference value.

One alternative for the quantification of PODXL protein in a sample, such as the sample earlier obtained from the subject or the reference sample, is the determination of the fraction of cells in the sample that exhibit PODXL protein expression over a certain level. The fraction may for example be: a "cellular fraction", wherein the PODXL protein expression of the whole cells is taken into account; a "cytoplasmic fraction", wherein the PODXL protein expression of only the cytoplasms of the cells is taken into account; or a "membranous fraction", wherein the PODXL protein expression of only the membranes of the cells is taken into account. The cellular, cytoplasmic or membranous fraction may for example be classified as <1%, 1-50%, >50% immunoreactive cells of the relevant cell population. The "membranous fraction" corresponds to the percentage of relevant cells in a sample that exhibits a positive staining in the membranes, wherein a distinct immunoreactivity in the membrane is considered positive and no immunoreactivity in the membranes is considered negative. The person skilled in the art of pathology understands which cells that are relevant under the conditions present when performing the method and may determine a cellular, cytoplasmic or membranous fraction based on his general knowledge and the teachings of the present disclosure. The relevant cells may for example be tumor cells or tumor cells at the invasive front.

Another alternative for the quantification of PODXL protein expression in a sample, such as the sample earlier obtained from the subject or the reference sample, is the determination of the overall staining intensity of the sample. The intensity may for example be: a "cellular intensity", wherein the PODXL protein expression of the whole cells is taken into account; a "cytoplasmic intensity", wherein the PODXL protein expression of only the cytoplasms of the cells is taken into account; or a "membranous intensity", wherein the PODXL protein expression of only the membranes of the cells is taken into account. Outcome of a membranous intensity determination may be classified as: absent=no overall immunoreactivity in the membranes of relevant cells of the sample, weak=faint overall immunoreactivity in the membranes of relevant cells of the sample, moderate=medium overall immunoreactivity in the membranes of relevant cells of the sample, or strong=distinct and strong overall immunoreactivity in the membranes of relevant cells of the sample. The person skilled in the art understands which cells that are relevant under the conditions present when performing the method and may determine a cellular, membranous or cytoplasmic intensity based on his general knowledge and the teachings of the present disclosure. The relevant cells may for example be tumor cells or tumor cells at the invasive front.

The inventors have found that membranous expression of PODXL protein is particularly relevant for establishing prognoses.

Thus, in embodiments of the methods of the above aspects, the reference value may be a membranous fraction, a membranous intensity or a combination thereof. Accordingly, the sample value may be a membranous fraction, a membranous intensity or a combination thereof.

For example, the reference value may be an absent or a weak membranous intensity. Also, the reference value may be a membranous fraction of 25% or lower, such as 20% or lower, such as 15% or lower, such as 10% or lower, such as 5% or lower, such as 2% or lower, such as 1% or lower, such as 0%.

In one embodiment, the sample value is classified as:
negative (0);
weak cytoplasmic positivity in any proportion of cells (1);
moderate cytoplasmic positivity in any proportion of cells (2);
distinct membranous positivity in 1-50% of cells (3); or
distinct membranous positivity in >50% of cells (4).

In such an embodiment, 2 may be a suitable reference value, which would mean that subjects exhibiting positive expression in the membranes are considered PODXL high.

The person skilled in the art realizes that various combinations or functions of fractions and intensities or other values may be used as the reference value within the framework of the present disclosure. Consequently, the reference value may involve two, and possibly even more, criteria.

In general, the selection of the reference value may depend on the staining procedure, e.g., on the employed anti-PODXL antibody and on the staining reagents.

Guided by the present disclosure, a person skilled in the art, e.g. a pathologist, understands how to perform the evaluation yielding a fraction, such as a cellular, cytoplasmic or membranous fraction, or an intensity, such as a cellular, cytoplasmic or membranous intensity. For example, the skilled artisan may use a reference sample comprising a predetermined amount of PODXL protein for establishing the appearance of a certain fraction or intensity.

However, a reference sample may not only be used for the provision of the actual reference value, but also for the provision of an example of a sample having an amount of PODXL protein, that is higher than the amount corresponding to the reference value. As an example, in histochemical staining, such as in immunohistochemical staining, the skilled artisan may use a reference sample for establishing the appearance of a stained sample having a high amount of PODXL protein or exhibiting membranous PODXL expression. Such a reference sample is thus a positive reference. Subsequently, the skilled artisan may assess the appearances of samples having lower amounts of PODXL protein, such as the appearance of a sample with an amount of PODXL protein corresponding to the reference value. In other words, the skilled artisan may use a reference sample to create a mental image of a reference value corresponding to an amount of PODXL protein which is lower than that of the reference sample. Alternatively, or as a complement, in such assessments, the skilled artisan may use another reference sample having a low amount of PODXL protein, or lacking detectable PODXL protein, for establishing the appearance of such sample, e.g., as a "negative reference".

For example, if a membranous fraction of 1% is used as the reference value, two reference samples may be employed: a first reference sample having no detectable PODXL protein; and a second reference sample having an amount of PODXL protein corresponding to a membranous fraction of at least 50%, which is higher than the reference value.

Consequently, in the evaluation, the skilled artisan may use a reference sample for establishing the appearance of a sample with a high amount of PODXL protein. Such reference sample may be a sample comprising tissue expressing a high amount of PODXL protein, such as a sample comprising bladder tumor tissue having a pre-established high expression of PODXL protein.

As mentioned above, cell lines expressing a controlled amount of PODXL protein may be used as the reference, in particular as a positive reference.

One or more pictures may also be provided as the "reference sample". For example, such a picture may show an example of a tumor tissue slide stained with a certain antibody during certain conditions exhibiting a certain membranous intensity and/or fraction. The above discussion about the "reference sample" applies mutatis mutandis to pictures.

In some embodiments, step a) of the methods of the above aspects may comprise:
obtaining biological material from the subject, excising or selecting a relevant part of the biological material to obtain said sample and optionally arranging the sample on a solid phase to facilitate the evaluation of step a). Step a) may thus, as an example, comprise obtaining tissue material from the bladder of said subject, optionally fixating the tissue material in paraffin or formalin, histo-processing the tissue material to obtain a section which constitute said sample and optionally mounting said sample on a transparent slide, such as a glass slide, for microscopy.

In embodiments of the methods of the aspects above, the PODXL protein may be detected and/or quantified through the application to the sample of a detectable and/or quantifiable affinity ligand, which is capable of selective interaction with the PODXL protein. The application of the affinity ligand is performed under conditions that enable binding of the affinity ligand to PODXL protein in the sample.

In more detail, step a) of some embodiments of the methods of the above aspects may comprise:
a1) applying to said sample a quantifiable affinity ligand capable of selective interaction with the PODXL protein to be evaluated, said application being performed under conditions that enable binding of said affinity ligand to PODXL protein present in said sample;
a2) removing non-bound affinity ligand; and
a3) quantifying the affinity ligand remaining in association with said sample to evaluate said amount.

"Affinity ligand remaining in association with the sample" refers to affinity ligand which was not removed in step a2), e.g., the affinity ligand bound to the sample. Here, the binding may for example be the interaction between antibody and antigen.

However, the removal of non-bound affinity ligand according to a2), e.g. the washing, is not always necessary. Thus, in some embodiments of the methods of the aspects above, step a) may comprise:
aI) applying to said sample a quantifiable affinity ligand capable of selective interaction with the PODXL protein to be evaluated, said application being performed under conditions that enable binding of said affinity ligand to PODXL protein present in said sample;

aII) quantifying the affinity bound to said sample to evaluate said amount.

In the context of the present disclosure, "specific" or "selective" interaction of e.g., an affinity ligand with its target or antigen means that the interaction is such that a distinction between specific and non-specific, or between selective and non-selective, interaction becomes meaningful. The interaction between two proteins is sometimes measured by the dissociation constant. The dissociation constant describes the strength of binding (or affinity) between two molecules. Typically the dissociation constant between an antibody and its antigen is from $10^{-7}$ to $10^{-11}$ M. However, high specificity/selectivity does not necessarily require high affinity. Molecules with low affinity (in the molar range) for its counterpart have been shown to be as selective/specific as molecules with much higher affinity. In the case of the present disclosure, a specific or selective interaction refers to the extent to which a particular method can be used to determine the presence and/or amount of a specific protein, the target protein, under given conditions in the presence of other proteins in a biological sample, such as a tissue sample or a fluid sample of a naturally occurring or processed biological fluid. In other words, specificity or selectivity is the capacity to distinguish between related proteins. For example, the specificity or selectivity of an antibody may be determined using a protein array set-up, a suspension bead array and a multiplexed competition assay, respectively (see e.g. Examples, section 2 of WO2011/051288). Specificity and selectivity determinations are also described in Nilsson P et al. (2005) Proteomics 5:4327-4337.

It is regarded as within the capabilities of those of ordinary skill in the art to select or manufacture the proper affinity ligand and to select the proper format and conditions for detection and/or quantification. Nevertheless, examples of affinity ligands that may prove useful, as well as examples of formats and conditions for detection and/or quantification, are given below for the sake of illustration.

Thus, in embodiments of the present disclosure, the affinity ligand may be selected from the group consisting of antibodies, fragments thereof and derivatives thereof. The affinity ligand may thus be based on an immunoglobulin scaffold. The antibodies and the fragments or derivatives thereof are normally isolated. Also, they may be antigen purified. Antibodies comprise monoclonal and polyclonal antibodies of any origin, including murine, rabbit, human and other antibodies, as well as chimeric antibodies comprising sequences from different species, such as partly humanized antibodies, e.g., partly humanized mouse antibodies. Polyclonal antibodies are produced by immunization of animals with the antigen of choice. Monoclonal antibodies of defined specificity can be produced using the hybridoma technology developed by Köhler and Milstein (Köhler G and Milstein C (1976) Eur. J. Immunol. 6:511-519). The antibody fragments and derivatives of the present disclosure are capable of selective interaction with the same antigen (e.g. PODXL protein) as the antibody they are fragments or derivatives of. Antibody fragments and derivatives comprise Fab fragments, consisting of the first constant domain of the heavy chain (CH1), the constant domain of the light chain (CL), the variable domain of the heavy chain (VH) and the variable domain of the light chain (VL) of an intact immunoglobulin protein; Fv fragments, consisting of the two variable antibody domains VH and VL (Skerra A and Pluckthun A (1988) Science 240:1038-1041); single chain Fv fragments (scFv), consisting of the two VH and VL domains linked together by a flexible peptide linker (Bird R E and Walker B W (1991) Trends Biotechnol. 9:132-137); Bence Jones dimers (Stevens F J et al. (1991) Biochemistry 30:6803-6805); camelid heavy-chain dimers (Hamers-Casterman C et al. (1993) Nature 363:446-448) and single variable domains (Cai X and Garen A (1996) Proc. Natl. Acad. Sci. U.S.A. 93:6280-6285; Masat L et al. (1994) Proc. Natl. Acad. Sci. U.S.A. 91:893-896), and single domain scaffolds like e.g., the New Antigen Receptor (NAR) from the nurse shark (Dooley H et al. (2003) Mol. Immunol. 40:25-33) and minibodies based on a variable heavy domain (Skerra A and Pluckthun A (1988) Science 240:1038-1041).

SEQ ID NO:1 was designed for immunizations, e.g., designed to lack transmembrane regions to ensure efficient expression in E. coli, and to lack any signal peptide, since those are cleaved off in the mature protein. Consequently, an antibody or fragment or derivative thereof according to the present disclosure may for example be one that is obtainable by a process comprising a step of immunizing an animal, such as a rabbit, with a protein whose amino acid sequence comprises, preferably consists of, the sequence SEQ ID NO:1. Alternatively, a peptide having the amino acid sequence SEQ ID NO:8 may be used for this purpose. Another alternative is a peptide having the amino acid sequence SEQ ID NO: 13 or SEQ ID NO: 14. For example, the immunization process may comprise primary immunization with the protein or peptide in Freund's complete adjuvant. Also, the immunization process may further comprise boosting at least two times, in intervals of 2-6 weeks, with the protein or peptide in Freund's incomplete adjuvant. Processes for the production of antibodies or fragments or derivatives thereof against a given target are known in the art.

In the context of the present disclosure, an "antigen purified antibody" is one or a population of polyclonal antibodies which has been affinity purified on its own antigen, thereby separating such antigen purified antibodies from other antiserum proteins and non-specific antibodies. This affinity purification results in antibodies that bind selectively to its antigen. In the case of the present disclosure, the polyclonal antisera are purified by a two-step immunoaffinity based protocol to obtain antigen purified antibodies selective for the target protein. Antibodies directed against generic affinity tags of antigen fragments are removed in a primary depletion step, using the immobilized tag protein as the capturing agent. Following the first depletion step, the serum is loaded on a second affinity column with the antigen as capturing agent, in order to enrich for antibodies specific for the antigen (see also Nilsson P et al. (2005) Proteomics 5:4327-4337).

Polyclonal and monoclonal antibodies, as well as their fragments and derivatives, represent the traditional choice of affinity ligands in applications requiring selective biomolecular recognition, such as in the detection and/or quantification of PODXL protein according to the method aspects above. However, those of skill in the art know that, due to the increasing demand of high throughput generation of selective binding ligands and low cost production systems, new biomolecular diversity technologies have been developed during the last decade. This has enabled a generation of novel types of affinity ligands of both immunoglobulin as well as non-immunoglobulin origin that have proven equally useful as binding ligands in biomolecular recognition applications and can be used instead of, or together with, immunoglobulins.

The biomolecular diversity needed for selection of affinity ligands may be generated by combinatorial engineering of one of a plurality of possible scaffold molecules, and specific and/or selective affinity ligands are then selected using a suitable selection platform. The scaffold molecule may be of immunoglobulin protein origin (Bradbury A R and Marks J D (2004) J. Immunol. Meths. 290:29-49), of non-immunoglobulin protein origin (Nygren P A and Skerra A (2004) J. Immunol. Meths. 290:3-28), or of an oligonucleotide origin (Gold L et al. (1995) Annu. Rev. Biochem. 64:763-797).

A large number of non-immunoglobulin protein scaffolds have been used as supporting structures in development of novel binding proteins. Non-limiting examples of such structures, useful for generating affinity ligands against PODXL protein for use according to the present disclosure, are staphylococcal protein A and domains thereof and derivatives of these domains, such as protein Z (Nord K et al. (1997) Nat. Biotechnol. 15:772-777); lipocalins (Beste G et al. (1999) Proc. Natl. Acad. Sci. U.S.A. 96:1898-1903); ankyrin repeat domains (Binz H K et al. (2003) J. Mol. Biol. 332:489-503); cellulose binding domains (CBD) (Smith G P et al. (1998) J. Mol. Biol. 277:317-332; Lehtiö J et al. (2000) Proteins 41:316-322); γ crystallines (Fiedler U and Rudolph R, WO01/04144); green fluorescent protein (GFP) (Peelle B et al. (2001) Chem. Biol. 8:521-534); human cytotoxic T lymphocyte-associated antigen 4 (CTLA-4) (Hufton S E et al. (2000) FEBS Lett. 475:225-231; Irving R A et al. (2001) J. Immunol. Meth. 248:31-45); protease inhibitors, such as Knottin proteins (Wentzel A et al. (2001) J. Bacteriol. 183:7273-7284; Baggio R et al. (2002) J. Mol. Recognit. 15:126-134) and Kunitz domains (Roberts B L et al. (1992) Gene 121:9-15; Dennis M S and Lazarus R A (1994) J. Biol. Chem. 269: 22137-22144); PDZ domains (Schneider S et al. (1999) Nat. Biotechnol. 17:170-175); peptide aptamers, such as thioredoxin (Lu Z et al. (1995) Biotechnology 13:366-372; Klevenz B et al. (2002) Cell. Mol. Life Sci. 59:1993-1998); staphylococcal nuclease (Norman T C et al. (1999) Science 285:591-595); tendamistats (McConell S J and Hoess R H (1995) J. Mol. Biol. 250:460-479; Li R et al. (2003) Protein Eng. 16:65-72); trinectins based on the fibronectin type III domain (Koide A et al. (1998) J. Mol. Biol. 284:1141-1151; Xu L et al. (2002) Chem. Biol. 9:933-942); and zinc fingers (Bianchi E et al. (1995) J. Mol. Biol. 247:154-160; Klug A (1999) J. Mol. Biol. 293:215-218; Segal D J et al. (2003) Biochemistry 42:2137-2148).

The above-mentioned examples of non-immunoglobulin protein scaffolds include scaffold proteins presenting a single randomized loop used for the generation of novel binding specificities, protein scaffolds with a rigid secondary structure where side chains protruding from the protein surface are randomized for the generation of novel binding specificities, and scaffolds exhibiting a non-contiguous hyper-variable loop region used for the generation of novel binding specificities.

In addition to non-immunoglobulin proteins, oligonucleotides may also be used as affinity ligands. Single stranded nucleic acids, called aptamers or decoys, fold into well-defined three-dimensional structures and bind to their target with high affinity and specificity. (Ellington A D and Szostak J W (1990) Nature 346:818-822; Brody E N and Gold L (2000) J. Biotechnol. 74:5-13; Mayer G and Jenne A (2004) BioDrugs 18:351-359). The oligonucleotide ligands can be either RNA or DNA and can bind to a wide range of target molecule classes.

For selection of the desired affinity ligand from a pool of variants of any of the scaffold structures mentioned above, a number of selection platforms are available for the isolation of a specific novel ligand against a target protein of choice. Selection platforms include, but are not limited to, phage display (Smith G P (1985) Science 228:1315-1317), ribosome display (Hanes J and Pluckthun A (1997) Proc. Natl. Acad. Sci. U.S.A. 94:4937-4942), yeast two-hybrid system (Fields S and Song 0 (1989) Nature 340:245-246), yeast display (Gai S A and Wittrup K D (2007) Curr Opin Struct Biol 17:467-473), mRNA display (Roberts R W and Szostak J W (1997) Proc. Natl. Acad. Sci. U.S.A. 94:12297-12302), bacterial display (Daugherty P S (2007) Curr Opin Struct Biol 17:474-480, Kronqvist N et al. (2008) Protein Eng Des Sel 1-9, Harvey B R et al. (2004) PNAS 101(25):913-9198), microbead display (Nord 0 et al. (2003) J Biotechnol 106:1-13, WO01/05808), SELEX (System Evolution of Ligands by Exponential Enrichment) (Tuerk C and Gold L (1990) Science 249:505-510) and protein fragment complementation assays (PCA) (Remy I and Michnick S W (1999) Proc. Natl. Acad. Sci. U.S.A. 96:5394-5399).

Thus, in embodiments of the present disclosure, the affinity ligand may be a non-immunoglobulin affinity ligand derived from any of the protein scaffolds listed above, or an oligonucleotide molecule.

The PODXL protein fragment SEQ ID NO:1 was designed to consist of a unique sequence with low homology with other human proteins and to minimize cross reactivity of generated affinity reagents. Consequently, in embodiments of the present disclosure, the affinity ligand may be capable of selective interaction with a polypeptide consisting of the sequence SEQ ID NO:1 "The affinity ligand capable of selective interaction with a polypeptide consisting of the sequence SEQ ID NO:1" is capable of distinguishing a SEQ ID NO:1 fragment from a fragment consisting of another, non-overlapping, part of the PODXL protein.

Nine epitope regions (SEQ ID NO:4-12) have been identified within SEQ ID NO:1. Thus, in embodiments of the present disclosure, the affinity ligand may be capable of selective interaction with a polypeptide consisting of 20 amino acids or less, such as 15 amino acids or less and comprising an amino acid sequence selected from SEQ ID NO:4-12. SEQ ID NO:4-9 are preferred.

A monoclonal antibody binding SEQ ID NO:8 has in comparisons to other antibodies been shown to be particularly beneficial for immunohistochemical evaluation of PODXL protein expression. Thus, in embodiments of the present disclosure, the affinity ligand may be capable of selective interaction with a polypeptide consisting of 50 amino acids or less, such as 25 amino acids or less, such as 20 amino acids or less, such as 15 amino acids or less and comprising the amino acid sequence SEQ ID NO:8.

The detection and/or quantification of the affinity ligand capable of selective interaction with the PODXL protein may be accomplished in any way known to the skilled person for detection and/or quantification of binding reagents in assays based on biological interactions. Accordingly, any affinity ligand described above may be used to quantitatively and/or qualitatively detect the presence of the PODXL protein. These "primary" affinity ligands may be labeled themselves with various markers or may in turn be detected by secondary, labeled affinity ligands to allow detection, visualization and/or quantification. This can be accomplished using any one or more of a multitude of labels, which can be conjugated to the affinity ligand capable of interaction with PODXL protein or to any secondary affinity ligand, using any one or more of a multitude of techniques known to the skilled person, and not as such involving any undue experimentation.

Non-limiting examples of labels that can be conjugated to primary and/or secondary affinity ligands include fluorescent dyes or metals (e.g., fluorescein, rhodamine, phycoerythrin, fluorescamine), chromophoric dyes (e.g., rhodopsin), chemiluminescent compounds (e.g., luminal, imidazole), bioluminescent proteins (e.g., luciferin, luciferase), and haptens (e.g., biotin). A variety of other useful fluorescers and chromophores are described in Stryer L (1968) Science 162:526-533 and Brand L and Gohlke J R (1972) Annu. Rev. Biochem. 41:843-868. Affinity ligands can also be labeled with enzymes (e.g., horseradish peroxidase, alkaline phosphatase, beta-lactamase), radioisotopes (e.g., $^{3}H$, $^{14}C$, $^{32}P$, $^{35}S$ or $^{125}I$) and particles (e.g., gold). In the context of the present disclosure, "particles" refer to particles, such as metal particles, suitable for labeling of molecules. Further, the affinity ligands may also be labeled with fluorescent semiconductor nanocrystals (quantum dots). Quantum dots have superior quantum yield and are more photostable compared to organic fluorophores and are therefore more easily detected (Chan et al. (2002) *Curr Opi Biotech.* 13: 40-46). The different types of labels can be conjugated to an affinity ligand using various chemistries, e.g., the amine reaction or the thiol reaction. However, other reactive groups than amines and thiols can be used, e.g., aldehydes, carboxylic acids and glutamine.

The method aspects above may be put to use in any of several known formats and set-ups, of which a non-limiting selection is discussed below.

In a set-up based on histology, the detection, localization and/or quantification of a labeled affinity ligand bound to its PODXL protein target may involve visualizing techniques, such as light microscopy or immunofluoresence microscopy. Other methods may involve the detection via flow cytometry or luminometry.

A biological sample, such as a tumor tissue sample, which has been removed from the subject, may be used for detection and/or quantification of PODXL protein. The biological sample may be an earlier obtained sample. If using an earlier obtained sample in a method, no steps of the method are practiced on the human or animal body. The affinity ligand may be applied to the biological sample for detection and/or quantification of the PODXL protein. This procedure enables not only detection of PODXL protein, but may in addition show the distribution and relative level of expression thereof. Thus, membranous protein expression may be distinguished from cytoplasmic or nuclear protein expression.

The method of visualization of labels on the affinity ligand may include, but is not restricted to, fluorometric, luminometric and/or enzymatic techniques. Fluorescence is detected and/or quantified by exposing fluorescent labels to light of a specific wavelength and thereafter detecting and/or quantifying the emitted light in a specific wavelength region. The presence of a luminescently tagged affinity ligand may be detected and/or quantified by luminescence developed during a chemical reaction. Detection of an enzymatic reaction is due to a color shift in the sample arising from a chemical reaction. Those of skill in the art are aware that a variety of different protocols can be modified for proper detection and/or quantification.

In embodiments of the methods of the above aspects, a biological sample may be immobilized onto a solid phase support or carrier, such as nitrocellulose or any other solid support matrix capable of immobilizing PODXL protein present in the biological sample applied to it. Some well-known solid state support materials useful in the present invention include glass, carbohydrate (e.g., Sepharose), nylon, plastic, wool, polystyrene, polyethene, polypropylene, dextran, amylase, films, resins, cellulose, polyacrylamide, agarose, alumina, gabbros and magnetite. After immobilization of the biological sample, a primary affinity ligand specific to PODXL protein may be applied, e.g., as described in the Examples below. If the primary affinity ligand is not labeled in itself, the supporting matrix may be washed with one or more appropriate buffers known in the art, followed by exposure to a secondary labeled affinity ligand and washed once again with buffers to remove unbound affinity ligands. Thereafter, selective affinity ligands may be detected and/or quantified with conventional methods. The binding properties for an affinity ligand may vary from one solid state support to the other, but those skilled in the art should be able to determine operative and optimal assay conditions for each determination by routine experimentation.

Consequently, in embodiments of the methods of the above aspects, the quantifiable affinity ligand of a1) or aI) may be detected using a secondary affinity ligand capable of recognizing the quantifiable affinity ligand. The quantification of a3) or aII) may thus be carried out by means of a secondary affinity ligand with affinity for the quantifiable affinity ligand. As an example, the secondary affinity ligand may be an antibody or a fragment or a derivative thereof.

As an example, one available method for detection and/or quantification of the PODXL protein is by linking the affinity ligand to an enzyme that can then later be detected and/or quantified in an enzyme immunoassay (such as an EIA or ELISA). Such techniques are well established, and their realization does not present any undue difficulties to the skilled person. In such methods, the biological sample is brought into contact with a solid material or with a solid material conjugated to an affinity ligand against the PODXL protein, which is then detected and/or quantified with an enzymatically labeled secondary affinity ligand. Following this, an appropriate substrate is brought to react in appropriate buffers with the enzymatic label to produce a chemical moiety, which for example is detected and/or quantified using a spectrophotometer, fluorometer, luminometer or by visual means.

As stated above, primary and any secondary affinity ligands can be labeled with radioisotopes to enable detection and/or quantification. Non-limiting examples of appropriate radiolabels in the present disclosure are $^{3}H$, $^{14}C$, $^{32}P$, $^{35}S$ or $^{125}I$. The specific activity of the labeled affinity ligand is dependent upon the half-life of the radiolabel, isotopic purity, and how the label has been incorporated into the affinity ligand. Affinity ligands are preferably labeled using well-known techniques (Wensel T G and Meares C F (1983) in: *Radioimmunoimaging and Radioimmunotherapy* (Burchiel S W and Rhodes B A eds.) Elsevier, New York, pp 185-196). A thus radiolabeled affinity ligand can be used to visualize PODXL protein by detection of radioactivity in vivo or ex vivo. Radionuclear scanning with e.g., gamma camera, magnetic resonance spectroscopy or emission tomography function for detection in vivo and ex vivo, while gamma/beta counters, scintillation counters and radiographies are also used ex vivo.

To perform the methods of the present disclosure, a kit may be employed. There is thus provided a kit for selecting a treatment or establishing a prognosis for a bladder cancer subject, which kit comprises a) a quantifiable affinity ligand capable of selective interaction with a PODXL protein;

b) reagents necessary for quantifying the amount of the quantifiable affinity ligand of a).

Various components of the kit according to the third aspect may be selected and specified as described above in connection with the method aspects of the present disclosure.

Thus, the kit according to the present disclosure comprises an affinity ligand against PODXL, as well as other means that help to quantify the specific and/or selective affinity ligand after they have bound specifically and/or selectively to the respective target proteins. For example, the kit may contain a secondary affinity ligand for detecting and/or quantifying a complex formed by the target protein and the affinity ligand. The kit may also contain various auxiliary substances other than the affinity ligand, to enable the kit to be used easily and efficiently. Examples of auxiliary substances include solvents for dissolving or reconstituting lyophilized protein components of the kit, wash buffers, substrates for measuring enzyme activity in cases where an enzyme is used as a label, target retrieval solution to enhance the accessibility to antigens in cases where paraffin or formalin-fixed tissue samples are used, and substances such as reaction arresters, e.g., endogenous enzyme block solution to decrease the background staining and/or counterstaining solution to increase staining contrast, that are commonly used in immunoassay reagent kits.

In embodiments of the kit aspect, the affinity ligand may be selected as described above in connection with the method aspects.

Following the findings presented above, the inventors have realized several uses for the PODXL protein or a fragment thereof.

Thus, as a third aspect of the present disclosure, there is provided a use of a PODXL protein as a prognostic marker for bladder cancer. The use may be ex vivo.

In a similar manner, there is provided a use of a PODXL protein as a marker of a relatively poor prognosis for a mammalian subject having a bladder cancer.

In the context of the present disclosure, "prognostic marker" refers to something material which presence indicates a prognosis. The marker may thus be a biomarker, such as a human protein.

In embodiments of the third aspect, the PODXL protein may be provided in a biological sample, such as a bladder tumor tissue sample, from a subject having a bladder cancer.

As a fourth aspect of the present disclosure, there is provided a use of a PODXL protein, or an antigenically active fragment thereof, for the production, selection or purification of a prognostic agent for establishing a prognosis for a mammalian subject having a bladder cancer. The use may be ex vivo.

In the context of the present disclosure, "prognostic agent" refers to an agent having at least one property being valuable in an establishment of a prognosis, e.g., a prognosis for a mammalian subject having a bladder cancer. For example, the prognostic agent may be capable of selective interaction with the prognostic marker.

The prognostic agent may thus be an affinity ligand capable of selective interaction with the PODXL protein or the antigenically active fragment thereof. Examples of such affinity ligands are discussed above in connection with the method aspects.

Guided by the teachings of the present disclosure, the person skilled in the art understands how to use the PODXL protein or fragment in the production, selection or purification of the prognostic agent. For example, the use may comprise affinity purification on a solid support onto which the PODXL protein has been immobilized. The solid support may for example be arranged in a column. Further, the use may comprise selection of affinity ligands having specificity for the PODXL protein using a solid support onto which the polypeptide has been immobilized. Such solid support may be well plates (such as 96 well plates), magnetic beads, agarose beads or sepharose beads. Further, the use may comprise analysis of affinity ligands on a soluble matrix, for example using a dextran matrix, or use in a surface plasmon resonance instrument, such as a Biacore™ instrument, wherein the analysis may for example comprise monitoring the affinity for the immobilized PODXL protein of a number of potential affinity ligands.

Also, for the production of the prognostic agent, the PODXL protein or an antigenically active fragment thereof may be used in an immunization of an animal.

Such use may be involved in a method comprising the steps:
i) immunizing an animal using the PODXL protein or antigenically an active fragment thereof as the antigen;
ii) obtaining serum comprising the prognostic agent from the immunized animal; and, optionally,
iii) isolating the prognostic agent from the serum.

Alternatively the steps following the first step may be:
ii') obtaining cells from the immunized animal, which cells comprise DNA encoding the prognostic agent,
iii') fusing the cells with myeloma cells to obtain at least one clone, and
iv') obtaining the prognostic agent expressed by the clone.

In embodiments of the third or fourth aspect, the amino acid sequence of the PODXL protein (or fragment thereof) may comprise or consist of a sequence selected from:
i) SEQ ID NO:1; and
ii) a sequence which is at least 85% identical to SEQ ID NO:1.

In some embodiments, sequence ii) is at least 90% identical, at least 91% identical, at least 92% identical, at least 93% identical, at least 94 identical, at least 95% identical, at least 96% identical, at least 97 identical, at least 98% identical or at least 99% identical to SEQ ID NO:1.

Further, in embodiments of the third or fourth aspect the amino acid sequence of the PODXL protein may comprise or consist of a sequence selected from:
i) SEQ ID NO:2 or 3; and
ii) a sequence which is at least 85% identical to SEQ ID NO:2 or 3.

In some embodiments, sequence ii) is at least 90% identical, at least 91% identical, at least 92% identical, at least 93% identical, at least 94 identical, at least 95% identical, at least 96% identical, at least 97 identical, at least 98% identical or at least 99% identical to SEQ ID NO:2 or 3.

Several antigenic subregions of SEQ ID NO:1 have been identified. Thus, in embodiments of the present disclosure, the "antigenically active fragment" may consist of 25 amino acids or less and comprise an amino acid sequence selected from SEQ ID NO:4-12. In further embodiments, the "antigenically active fragment" may consist of 20 amino acids or less, such as 15 amino acids or less. SEQ ID NO:8 is preferred, as discussed above. SEQ ID NO:13 and 14 are also preferred, as shown below in Examples, Sections 4 and 5.

As a fifth aspect of the present disclosure, there is provided an affinity ligand capable of selective interaction with a PODXL protein.

Different embodiments of such an affinity ligand are discussed above in connection with the method aspects.

As a sixth aspect of the present disclosure, there is provided a use of an affinity ligand according to the fourth aspect as prognostic agent for bladder cancer. Consequently, the affinity ligand may be used for establishing a prognosis for a bladder cancer subject.

As a configuration of the sixth aspect, there is provided a use of an affinity ligand according to the fourth aspect for selecting a bladder cancer treatment. Such use may for example be performed ex vivo, e.g., involving the determination of the amount of PODXL in at least part of a sample earlier obtained from the subject.

EXAMPLES

1. Bladder Cancer TMA, Cohort I a) Material and Methods

This cohort is a consecutive cohort of all patients with a first diagnosis of urothelial cancer in the Department of Pathology, Skåne University Hospital, Malmö, from Oct. 1, 2002 until Dec. 31, 2003, for whom archival tumor specimens could be retrieved (n=110). The cohort includes 80 (72.7%) men and 30 (27.3%) women with a median age of 72.86 (39.25-89.87) years.

Information on vital status was obtained from the Swedish Cause of Death Registry up until Dec. 31, 2010. Follow-up started at date of diagnosis and ended at death, emigration or Dec. 31, 2010, whichever came first. Median follow-up time was 5.92 years (range 0.03-8.21) for the full cohort and 7.71 years (range 7.04-8.21) for patients alive at Dec. 31, 2010 (n=48). 48 patients (43.6%) died within 5 years.

The distribution of T-stage was 48 (43.6%) pTa, 24 (21.8%) pT1, 37(33.8) pT2 and 1(0.9%) pT3. 18 (16.4%) tumors were Grade I, 34(30.9%) Grade II and 58 (52.7%) Grade III. Permission for this study was obtained from the Ethics Committee at Lund University.

All tumors were histopathologically re-evaluated and classified according to the WHO grading system of 2004 by a board certified pathologist. Tissue microarrays (TMAs) were constructed using a semi-automated arraying device (TMArrayer, Pathology Devices, Westminister, Md., USA). All tumor samples were represented in duplicate tissue cores (1 mm).

For the immunohistochemical analysis of PODXL, four µm TMA-sections were automatically pretreated using the PT-link system (DAKO, Copenhagen, Denmark) and then stained in an Autostainer Plus (DAKO, Copenhagen, Denmark) with a polyclonal antibody targeting PODXL (HPA002210, Atlas Antibodies, Stockholm, Sweden) diluted 1:250.

PODXL expression was recorded as negative (0), weak cytoplasmic positivity in any proportion of cells (1), moderate cytoplasmic positivity in any proportion (2), distinct membranous positivity in 1-50% of cells (3) and distinct membranous positivity in >50% of cells (4). PODXL staining was evaluated by two independent observers who were blinded to clinical and outcome data.

Spearman's rho and Chi-square tests were applied for analysis of the correlation between PODXL expression and clinicopathological characteristics. Kaplan-Meier analysis and log rank test were used to illustrate differences in 5-year overall survival (OS) in strata according to PODXL expression. Cox regression proportional hazards modeling was used to estimate the impact of membranous vs. non-membranous PODXL expression on PFS, DSS and 5-year OS in both univariable and multivariable analysis, adjusted for age, sex, T-stage and grade. All tests were two sided. A p-value of 0.05 was considered significant. All statistical analyses were performed using IBM SPSS Statistics version 20.0 (SPSS Inc., Chicago, Ill., USA).

b) Results

Following antibody optimization and staining, PODXL expression could be evaluated in tumors from 103/110 (93.6%) cases. Membranous PODXL expression was predominantly observed in subsets of tumor cells at the leading invasive front, and was found in 16/103 (15.5%) of cases. None of the Ta tumors had membranous PODXL expression.

Analyses of the relationship between PODXL staining and established clinicopathological factors revealed strong, significant associations between membranous PODXL staining and more advanced T-stage and high grade tumors.

Kaplan-Meier analysis and log-rank test revealed a significantly reduced OS (logrank p<0.001, FIG. 1) for patients with tumors with membranous PODXL expression (score 3-4) compared to patients whose tumors did not express PODXL in the membrane (score 0-2). These associations were confirmed in Cox univariable analysis (HR=4.56; 95% CI=2.36-8.84), and remained significant in multivariable analysis adjusted for age, gender, T-stage and grade (HR=2.40; 95% CI=1.15-5.00), see Table 1.

Figure 2B:
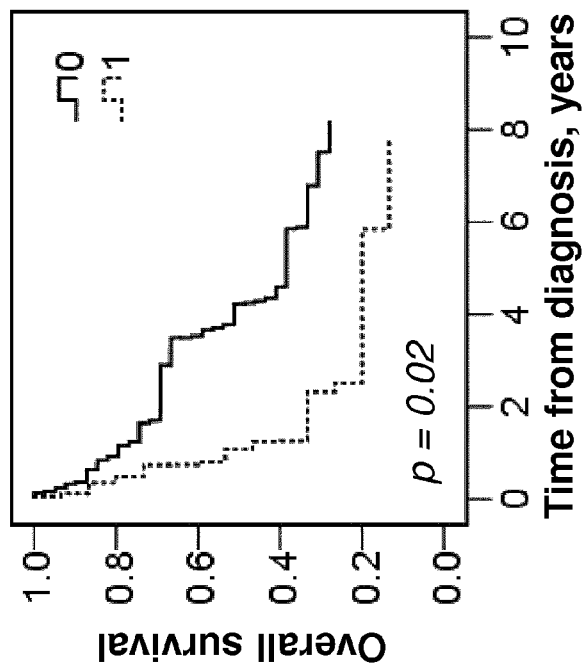
FIG. 2B shows patients diagnosed with grade 3 urothelial cancer, i.e. 53 subjects.
Figure 2A:
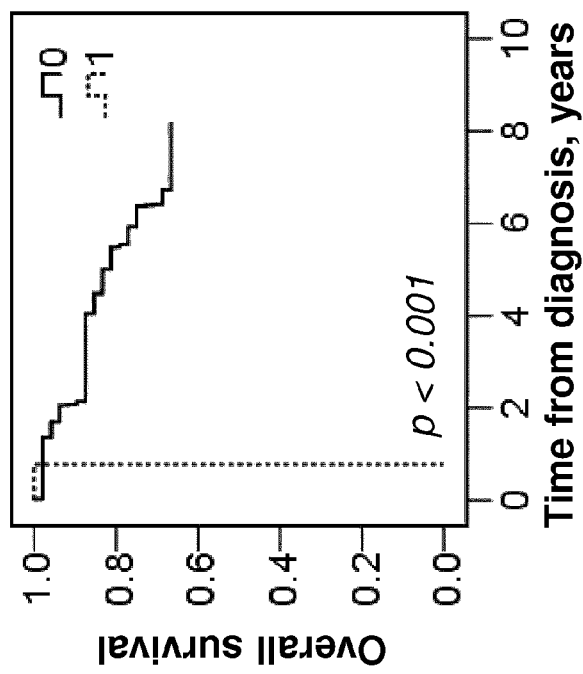
FIG. 2A shows patients diagnosed with grade 1 or 2 urothelial cancer, i.e. 49 subjects.

When analyzing grade 1 and 2 tumors only (FIG. 2A), there was still a significantly reduced OS for patients with tumors expressing membranous PODXL (score 3-4) compared to patients whose tumors did not express PODXL in the membrane (score 0-2). A similar correlation could also be seen for grade 3-tumors (FIG. 2B).

Figure 3A:
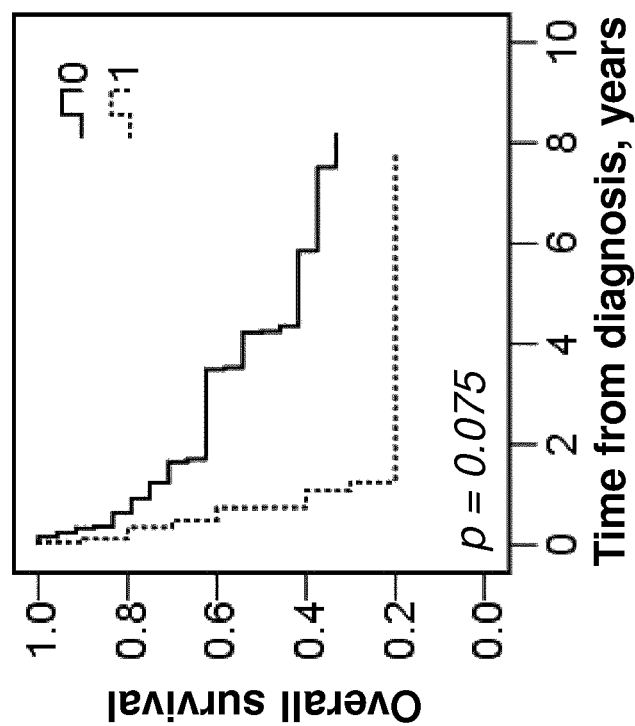
FIG. 3A shows patients diagnosed with stage T1 urothelial cancer, i.e. 24 subjects.
Figure 3B:
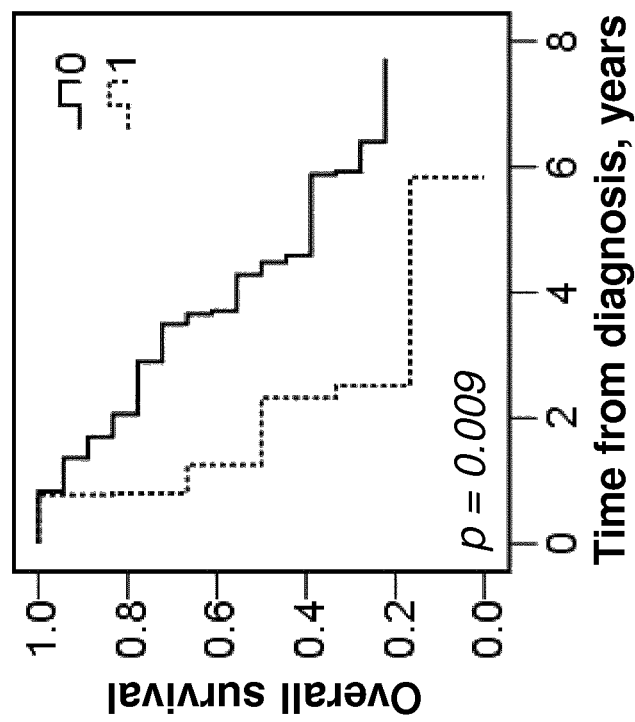
FIG. 3B shows patients diagnosed with stage T2 urothelial cancer, i.e. 34 subjects.
Figure 4:
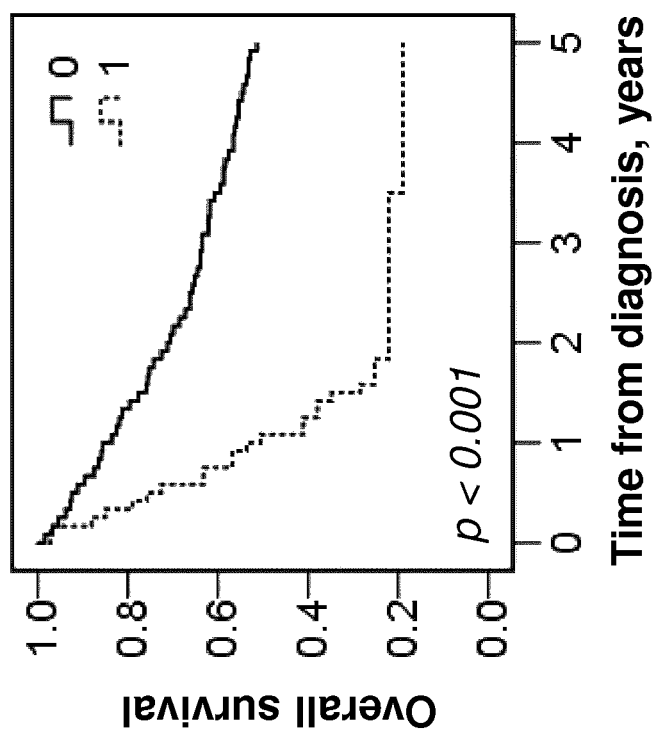
FIG. 4 shows the impact of membranous PODXL expression on 5-year overall survival (OS) of all patients in cohort II, i.e. 343 subjects, diagnosed with urothelial cancer. Patients were divided into two groups based on PODXL expression. The solid line represents patients with tumors without membranous PODXL expression, and the dotted line represents patients with tumors expressing membranous PODXL.

When analyzing stage T1 tumors separately, the OS of patients with stage T1 tumors expressing membranous PODXL was significantly reduced compared to patients with stage T1 tumors not expressing membranous PODXL (FIG. 3A). A similar trend could be seen for patients with stage T2 tumors (FIG. 3B).

2. Bladder Cancer TMA, Cohort II a) Material and Methods

This cohort includes 344 patients from a prospective cohort with newly diagnosed urinary bladder cancer at Uppsala University Hospital from 1984 up until 2005. Tumor specimens have been collected retrospectively and the predominant group of pTa tumors reduced to include 115 cases. Progression-free survival (PFS), overall survival (OS) and disease-specific survival (DSS) were calculated from the date of surgery to date of event or last follow-up. At follow up, patients with non-muscle invasive tumors were categorized as having none, few, or frequent recurrences. Definition of few recurrences was less than three recurrent tumors within 18 months, whereas frequent recurrences were three or more recurrences within the same time period. Progression was defined as shift of the tumor into a higher stage. Median time to progression for patients with non-muscle invasive disease was 18.0 months (range 2.0-55.0). Follow-up time for non-recurrent and non-progressing cases was and 5 years, respectively. Permission for this study was obtained from the Ethics Committee at Uppsala University.

TMA construction and immunohistochemical analysis were performed as described for cohort I in Section I above.

Spearman's rho and Chi-square tests were applied for analysis of the correlation between PODXL expression and clinicopathological characteristics. Kaplan-Meier analysis and log rank test were used to illustrate differences in progression free survival (PFS), disease-specific survival (DSS), and 5-year overall survival (OS) in strata according to PODXL expression. Cox regression proportional hazards modeling was used to estimate the impact of membranous vs non-membranous PODXL expression on PFS, DSS and 5-year OS in both univariable and multivariable analysis, adjusted for age, sex, T-stage and grade. All tests were two sided. A p-value of 0.05 was considered significant. All statistical analyses were performed using IBM SPSS Statistics version 20.0 (SPSS Inc., Chicago, Ill., USA).

b) Results

Following antibody optimization and staining, PODXL expression could be evaluated in tumors from 343/344 (99.7%) cases. Membranous PODXL expression was predominantly observed in subsets of tumor cells at the leading invasive front, and was found in 35/343 (10.2%) of cases. Only one Ta tumor had membranous PODXL expression.

Analyses of the relationship between PODXL staining and and established clinicopathological factors revealed strong, significant associations between membranous PODXL staining and more advanced T-stage and high grade tumors.

Kaplan-Meier analysis and log-rank test revealed a significantly reduced 5-year OS (logrank p<0.001, FIG. 4) for tumors with membranous PODXL expression (score 3-4) compared with tumors not expressing PODXL in the membrane (score 0-2). These associations were confirmed in Cox univariable analysis (HR=3.10; 95% CI=2.03-4.72), and remained significant in multivariable analysis adjusted for age, gender, T-stage and grade (HR=2.18; 95% CI=1.39-3.41), see Table 2. As can be seen in FIG. 5, significantly reduced 5-year OS (logrank p<0.001) for patients with tumors with membranous PODXL expression compared to patients with tumors not expressing PODXL in the membrane, could still be seen when analyzing low—(FIG. 5A), and high—(FIG. 5B) grade tumors separately. Likewise, the OS of the patients with tumors with membranous PODXL expression was Membranous PODXL expression was also associated with a significantly reduced PFS and DSS, as visualized in FIG. 7 (logrank p<0.001 for both) with an unadjusted HR=4.36; 95% CI=2.67-7.10, and adjusted HR=2.70; 95% CI=1.60-4.55 (Table 2).

The association between PODXL expression, disease progression within 24 months and 5-year OS in patients with Ta and T1 tumors was examined (Table 3). Despite the low number of cases with membranous PODXL expression in this patient category, membranous PODXL expression was an independent predictor of an increased risk of disease progression (univariable HR=6.19; 95% CI=1.42-26.98 and multivariable HR=4.60; 95% CI=1.04-20.39). Moreover, membranous PODXL expression was an independent predictor of an increased risk of death from disease (univariable HR=8.34; 95% CI=3.21-21.65 and multivariable HR=7.16; 95% 01=2.72-18.81).

TABLE 1

Relative risks of death from disease and overall death within 5 years according to clinicopathological factors and PODXL expression in Cohort I.

| | | Cohort I Risk of death within 5 years | |
|---|---|---|---|
| | n(events) | Univariable HR(95% CI) | Multivariable HR(95% CI) |
| Age | | | |
| Continuous | 103(45) | 1.05(1.02-1.08) | 1.05(1.01-1.08) |
| Gender | | | |
| Female | 28(12) | 1.00 | 1.00 |
| Male | 75(33) | 0.93(0.48-1.80) | 1.17(0.57-2.40) |
| Stage | | | |
| Ta | 44(6) | 1.00 | 1.00 |
| T1 | 24(16) | 6.36(2.48-16.32) | 3.61(1.34-9.70) |
| T2-4 | 35(23) | 8.07(3.27-19.87) | 5.84(2.31-14.79) |
| Grade | | | |
| Low | 49(9) | 1.00 | 1.00 |
| High | 54(36) | 5.34(2.56-11.11) | 1.60(0.56-4.57) |
| PODXL expression | | | |
| Negative | 87(32) | 1.00 | 1.00 |
| Positive | 16(13) | 4.56(2.36-8.84) | 2.47(1.26-4.86) |

TABLE 2

Relative risks of death from disease and overall death within 5 years according to clinicopathological factors and PODXL expression in Cohort II

| | Cohort II | | | | | |
|---|---|---|---|---|---|---|
| | Risk of death from disease | | | Risk of death within 5 years | | |
| | N (events) | Univariable HR (95% CI) | Multivariable HR (95% CI) | N (events) | Univariable HR (95% CI) | Multivariable HR (95% CI) |
| Age | | | | | | |
| Continuous | 300 (101) | 1.04 (1.02-1.07) | 1.05 (1.03-1.07) | 343 (170) | 1.06 (1.05-1.08) | 1.07 (1.05-1.09) |
| Gender | | | | | | |
| Female | 72 (28) | 1.00 | 1.00 | 83 (40) | 1.00 | 1.00 |
| Male | 228 (73) | 0.80 (0.52-1.24) | 1.00 (0.64-1.56) | 260 (130) | 0.97 (0.68-1.39) | 1.22 (0.85-1.76) |
| Stage | | | | | | |
| Ta | 104 (13) | 1.00 | 1.00 | 115 (35) | 1.00 | 1.00 |
| T1 | 97 (25) | 2.20 (1.13-4.31) | 2.15 (1.10-4.22) | 115 (52) | 1.62 (1.05-2.48) | 1.57 (1.02-2.41) |
| T2-4 | 99 (63) | 8.93 (4.90-16.27) | 7.56 (4.09-13.97) | 113 (83) | 4.35 (2.92-6.48) | 3.88 (2.57-5.86) |
| Grade | | | | | | |
| Low | 75 (7) | 1.00 | 1.00 | 82 (20) | 1.00 | 1.00 |
| High | 225 (94) | 5.79 (2.68-12.49) | 1.53 (0.59-3.94) | 261 (150) | 3.10 (1.94-4.95) | 1.20 (0.68-2.12) |

TABLE 2-continued

Relative risks of death from disease and overall death within 5 years according to clinicopathological factors and PODXL expression in Cohort II

| | Cohort II | | | | | |
|---|---|---|---|---|---|---|
| | Risk of death from disease | | | Risk of death within 5 years | | |
| | N (events) | Univariable HR (95% CI) | Multi-variable HR (95% CI) | N (events) | Univariable HR (95% CI) | Multi-variable HR (95% CI) |
| PODXL expression | | | | | | |
| Negative | 269 (80) | 1.00 | 1.00 | 308 (144) | 1.00 | 1.00 |
| Positive | 31 (21) | 4.36 (2.67-7.10) | 2.70 (1.60-4.55) | 35 (26) | 3.10 (2.03-4.72) | 2.18 (1.39-3.41) |

TABLE 3

Relative risks of disease progression within 24 months and disease specific survival according to clinicopathological factors and PODXL expression in patients with Ta-T1 tumors

| | Risk of disease progression within 24 months | | | Risk of death from disease | | |
|---|---|---|---|---|---|---|
| | N (events) | Univariable HR (95% CI) | Multi-variable HR (95% CI) | N (events) | Univariable HR (95% CI) | Multi-variable HR (95% CI) |
| Age | | | | | | |
| Continuous | 133 (19) | 1.02 (0.98-1.07) | 1.01 (0.97-1.06) | 201 (38) | 1.03 (1.00-1.06) | 1.03 (1.00-1.06) |
| Gender | | | | | | |
| Female | 29 (2) | 1.00 | 1.00 | 38 (5) | 1.00 | 1.00 |
| Male | 104 (17) | 2.51 (0.58-10.9) | 2.00 (0.46-8.81) | 163 (33) | 1.81 (0.70-4.65) | 1.38 (0.53-3.63) |
| Stage | | | | | | |
| Ta | 68 (7) | 1.00 | 1.00 | 104 (13) | 1.00 | 1.00 |
| T1 | 65 (12) | 1.93 (0.76-4.91) | 1.31 (0.48-3.6) | 97 (25) | 2.33 (1.19-4.56) | 2.29 (1.16-4.5) |
| Grade | | | | | | |
| Low | 48 (3) | 1.00 | 1.00 | 74 (7) | 1.00 | 1.00 |
| High | 85 (16) | 3.28 (0.96-11.) | 2.96 (0.85-10.31) | 127 (31) | 3.04 (1.33-6.92) | 1.59 (0.59-4.31) |
| PODXL expression | | | | | | |
| Non-membranous | 130 (17) | 1.00 | 1.00 | 194 (33) | 1.00 | 1.00 |
| Membranous | 3 (2) | 6.19 (1.42-27.0) | 4.60 (1.04-20) | 7 (5) | 8.34 (3.21-21.7) | 7.16 (2.7-18.8) |

3) Generation of Monoclonal Antibodies a) Materials and Methods

The purified fragment SEQ ID NO:1, obtained as described in Examples, section 1 of WO2011051288 was used as antigen for production of monoclonal antibodies. Antigen was sent to AbSea Biotechnology Ltd (Beijing, China) and briefly, the antigen was injected subcutaneously into BALB/c mice (4-6 weeks old, female) at three week intervals. The antigen was mixed with complete Freund's adjuvant for the first injection and incomplete Freund's adjuvant for the following injections. Three days before fusion, the mouse was last challenged with antigen intravenously. Hybridomas were generated by fusion of mouse splenocytes with the Sp2/0 myeloma cell line. By screening several cell lines using ELISA, cells that secreted antibodies specific for the antigen (SEQ ID NO:1) were identified and delivered to Atlas Antibodies AB for further characterization. Cell lines that showed positive results in ELISA, Western blot (WB) and immunohistochemistry (IHC) were selected for subcloning, performed by AbSea Biotechnology Ltd.

In addition, the immunohistochemical staining patterns of the monoclonal antibodies were compared to that of the monoclonal anti-PODXL antibody AMAb90667 (Atlas Antibodies, Stockholm, Sweden) described in Examples, sections 8 to 12 of US2012219548 (there denoted 8F6).

b) Results

Cell-lines were screened by ELISA (at AbSea) to identify lines that produce monoclonal antibodies (mAbs) that recognize the antigen (SEQ ID NO:1), but not the affinity tag His-ABP. 167 cell-lines showed specific binding to the antigen SEQ ID NO:1 in ELISA and were selected for further testing. For each of the selected clones 150-300 μl supernatant was collected, azide was added, and the supernatants were delivered to Atlas Antibodies AB on wet ice. The supernatants were stored at +4° C. upon arrival according to the instructions from AbSea. Further testing of the cell lines resulted in the identification of two interesting cell lines, clones CL0284 and CL0285, that gave positive results in both Western blot and IHC analysis. These clones were selected for subcloning and expansion, performed by AbSea Biotechnology Ltd.

4) Epitope Mapping Using Bioplex a) Synthetic Peptide Preparation

A PEPscreen library consisting of 26 biotinylated peptides corresponding to the protein fragment SEQ ID NO:1 of the PODXL protein (SEQ ID NO:2 or SEQ ID NO:3) was synthesized by Sigma-Genosys (Sigma-Aldrich). The peptides were 15 amino acids long with a 10 amino acid overlap, together covering the entire PrEST sequence (SEQ ID NO:1). The peptides were resolved in 80% DMSO to a final concentration of 10 mg/ml.

b) Bead Coupling

Neutravidin (Pierce, Rockford, Ill.) was immobilized on carboxylated beads (BioPlex COOH Beads, BioRad) in accordance to the manufacturer's protocol. Coupling of $10^6$ beads was performed using a filter membrane bottomed microtiter plate (MultiScreen-HTS, Millipore, Billerica, Mass.) as previously described (Larsson et al (2009) J Immunol Methods 15; 34(1-2):20-32, Schwenk et al (2007) Mol Cell Proteomics 6(1) 125:32). 26 distinct groups of beads with different color code IDs were activated using 1-Ethyl-3-(3-dimethylamino-propyl) carbodiimide and N-Hydroxysuccinimide. Neutravidin (250 μg/ml in 50 mM Hepes pH 7.4) was added to the beads and incubated for 120 min on a shaker. The beads were finally washed, re-suspended, and transferred to micro-centrifuge tubes for storage at 4° C. in PBS-BN (1×PBS, 1% BSA, 0.05% NaN3). The biotinylated peptides were diluted in PBS-BN to a concentration of 0.1 mg/ml, and 50 μl of each peptide was used in the coupling reaction, which was conducted for 60 min with shaking at RT. Finally, the beads were washed with 3×100 μl PBS-BN buffer and stored at 4° C. until further use.

c) Determination of Binding Specificity

A bead mixture containing all 26 bead IDs was prepared and 10 μl of mouse anti-PODXL, obtained as described in section 2, was mixed with 30 μl of the bead mix and incubated for 60 min at RT. A filter bottomed microtiter plate (Millipore) was utilized for washing and following each incubation all wells were washed with 2×100 μl PBS-BN. To the beads, 25 μl of R-Phycoerythrine labeled anti-mouse IgG antibody (Jackson ImmunoResearch) were added for a final incubation of 30 min at RT.

Measurements were performed using the Bioplex 200 Suspension Array instrumentation with Bio-Plex Manager 5.0 software. For each experiment, 50 events per bead ID were counted and the median fluorescence intensity (MFI) was used as a measurement of antibody binding to individual bead populations.

d) Results

The specificities of the monoclonal anti-PODXL antibodies with clone ID:s CL0284 and CL0285 were tested in an assay using beads coupled with synthetic biotinylated peptides. The monoclonal antibody CL0284 reacted with peptide 13, corresponding to one distinct region on the PrEST sequence, sequence SEQ ID NO: 13 The monoclonal antibody CL0285 reacted with peptide 23, corresponding to one distinct region on the PrEST sequence, sequence SEQ ID NO: 14.

5) Evaluation of Antibodies for IHC-Analysis a) Material and Methods

Tissue sections from urothelial cancer samples, from the cohort described in Example 1 above, were used for evaluation of the monoclonal anti-PODXL antibodies CL0284 and CL0285, obtained as described in Example 3 above. For reference, the monoclonal anti-PODXL antibody 8F6, described in Examples, sections 8 to 12 of US2012219548, was included in the evaluation. Automated immunohistochemistry was performed as previously described (Kampf C et al (2004) Clin. Proteomics 1:285-300). In brief, the glass slides were incubated for over night in 50° C., de-paraffinized in xylene (2×5 min+1×1 min) and hydrated in graded alcohols. During hydration, endogenous peroxidase was blocked with $H_2O_2$ (Merck). For antigen retrieval, slides were immersed in Citrate buffer pH 6 (PT Module Buffer 1, 100×-citrate buffer pH=6, Thermo Fisher Scientific) and boiled for 4 min at 125° C. in a Decloaking Chamber® (Biocare Medical). Slides were placed in the Lab Vision Autostainer 480® (Thermo Fisher Scientific) and incubated for 30 min at room temperature with the primary antibody. Slides were then incubated for 20-30 min at room temperature with Primary Antibody Enhancer (Thermo Fisher Scientific), followed by incubation with HRP Polymer (UltraVision LP detection system, Thermo Fisher Scientific)® for 30 min at room temp. Between all steps, slides were rinsed in wash buffer (ThermoFisher Scientific). Finally, diaminobenzidine (Thermo Fisher Scientific) was used as chromogen and Mayer's hematoxylin (Histolab) was used for counterstaining. The slides were mounted with Pertex® (Histolab). All images of immunohistochemically stained tissue were manually evaluated under the microscope.

b) Results

The staining patterns for the monoclonal anti-PODXL antibodies CL0284 and CL0285 were evaluated by two independent observers and compared to the staining pattern for the monoclonal anti-PODXL antibody 8F6. The antibodies CL0284 and CL0285 were found by both observers to have an identical staining pattern as the 8F6 antibody, and the stainings of CL0284 and CL0285 were also found to be as distinct as the staining of the 8F6 antibody. The 8F6 antibody has in an earlier comparative study been shown to be superior to several other antibodies tested, see Examples section 12 of US2012219548.

A Non-Limiting Example of an Establishment of a Prognosis

Following the establishment of a bladder cancer diagnosis in a patient, a tumor tissue sample from the patient is obtained from a transurethral resection. For the provision of a "negative reference", a sample is taken from archival bladder cancer tissue material essentially lacking PODXL protein expression in the membranes of the tumor cells. Further, for the provision of a "positive reference", a sample is taken from archival bladder tumor tissue material showing membranous PODXL expression in at least 50% of the tumor cells Sample material from the patient and the archival tissue are fixated in buffered formalin and histo-processed in order to obtain thin sections (4 µm) of the sample material. Alternatively, the archival material is already prepared in this way.

Immunohistochemistry is performed in accordance with the above. One or more sample sections from each sample is/are mounted on glass slides that are incubated for 45 min in 60° C., de-paraffinized (if the sample in question was paraffinized) in xylene (2×15 min) and hydrated in graded alcohols. For antigen retrieval, slides are immersed in TRS (Target Retrieval Solution, pH 6.0, DakoCytomation) and boiled for 4 min at 125° C. in a Decloaking Chamber® (Biocare Medical). Slides are placed in the Autostainer® (DakoCytomation) and endogenous peroxidase is initially blocked with $H_2O_2$ (DakoCytomation). The reason for mounting multiple sample sections is to increase the accuracy of the results.

An antigen purified polyclonal antibody targeting the PODXL subsequence SEQ ID NO:1 (HPA002210, Atlas Antibodies, Stockholm, Sweden) diluted 1:250 is added to the slides, which are incubated for 30 min in room temperature, followed by 30 min of incubation in room temperature with a labeled secondary antibody; e.g. goat-anti-peroxidase (rabbit or mouse) conjugated Envision®. Alternatively, the primary antibody may be a monoclonal antibody capable of selective interaction with SEQ ID NO.8. To detect the secondary antibody, diaminobenzidine (DakoCytomation) is used as chromogen, contrasted with a Harris hematoxylin (Sigma-Aldrich) counterstaining. Between all steps, slides are rinsed in wash buffer (DakoCytomation). The slides are then mounted with Pertex® (Histolab) mounting media.

As a tool to validate the staining procedure, two control cell-lines may be used; e.g. one slide with cells expressing PODXL protein (positive cell line) and one slide having cells with no PODXL protein expression (negative cell line). The skilled artisan understands how to provide such cell lines, for example guided by the disclosure of Rhodes et al. (2006) The biomedical scientist, p 515-520. The control-line slides may be simultaneously stained in the same procedure as the other slides, i.e. incubated with the same primary and secondary antibodies.

For example, the tumor tissue slides from the subject, the staining reference slides, and optionally, the slides with control cell-lines, may be scanned in a light microscope using a ScanScope T2 automated slide scanning system (Aperio Technologies) at ×20 magnification. However, this scanning step is not necessary, but may make the procedure easier if, for example, the preparation and staining of the slides and the evaluation of the stained slides (see below) are performed at different locations or by different persons.

If control cell-lines are used, these are inspected to validate the staining procedure. If the cell-lines display staining results outside acceptable criteria, e.g. staining artifacts recognized by the skilled artisan, the staining of the tissue samples is considered invalid and the whole staining procedure is repeated with new slides. If the positive and negative cell-lines display the expected staining patterns, the staining is considered as valid.

The stained sample slide(s) from the tumor tissue sample from the patient is/are manually evaluated by visual inspection, and for each slide it is determined if PODXL is expressed in the membranes of the tumor cells or not. The person performing the evaluation and determination is aided by visual inspection of the stained positive and negative reference slides.

It is thus determined if the patient belongs to the group having the membranous expression or the group lacking it. The prognoses of the respective groups may be read from dichotomized data as those presented in the figures, wherein the upper curve represents the group of patients having the relatively good prognosis and the lower curve represents the group of patients having the relatively poor prognosis. For example, the relatively good prognosis may be an average five-year overall survival of about 62% and the relatively poor prognosis may be an average five-year overall survival of about 19% (FIG. 1).

If the cancer of the subject is diagnosed as early stage (i.e. Ta or T1), the respective prognoses may be read from dichotomized data exclusively based on subjects having such early stage cancers, such as in FIG. 6 (good and poor prognosis: about 61% and about 15%, respectively). It may be decided to refrain from any additional treatment (TUR-B, which is curative, has already been performed) if the patient belongs to the group of the good prognosis. If the patient belongs to the other group, radical cystectomy, chemotherapy and/or BCG may be performed even though a Ta or T1 patient is normally not treated this way.

All cited material, including but not limited to publications, DNA or protein data entries, and patents, referred to in this application are herein incorporated by reference.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. Method of treatment of a subject having a stage Ta or T1 bladder cancer with elevated PODXL expression, comprising the steps of:
   a) evaluating an amount of PODXL in at least part of a sample earlier obtained from the subject and determining a sample value corresponding to the evaluated amount;
   b) comparing said sample value with a predetermined reference value; and
   treating said subject with a treatment selected from the group consisting of chemotherapy, *Bacillus* Calmette-Guerin (BCG) treatment and primary cystectomy, wherein said sample value is higher than said reference value.

2. Method of treatment of a subject having an invasive bladder cancer with elevated PODXL expression, comprising the steps of:
   a) evaluating an amount of PODXL in at least part of a sample earlier obtained from the subject and determining a sample value corresponding to the evaluated amount;
   b) comparing said sample value with a predetermined reference value; and
   c) applying a treatment selected from the group consisting of chemotherapy, biological treatment and radiation therapy,
   wherein said sample value is higher than said reference value.

3. Method according to claim 2, wherein the chemotherapy is neo-adjuvant.

4. Method according to claim 1, wherein the bladder cancer is of grade 1 or 2.

5. Method according to claim 1, wherein said sample comprises tumor cells from said subject.

6. Method according to claim 1, wherein the evaluation of step a) is limited to the membranes of tumor cells of the sample.

7. Method according to claim 1, wherein the reference value of step b) corresponds to a reference sample having no detectable membranous PODXL protein in tumor cells.

8. Method according to claim 1, wherein said sample is a bladder tumor tissue sample.

9. Method according to claim 1, wherein step a) comprises:
   aI) applying to said sample of step a) a quantifiable antibody capable of selective interaction with the PODXL protein to be evaluated, said application being performed under conditions that enable binding of the antibody to PODXL protein present in the sample; and aII) quantifying the antibody bound to said sample to evaluate said amount.

10. Method according to claim 9, wherein said quantifiable antibody is capable of selective interaction with a peptide whose amino acid sequence consists of the sequence SEQ ID NO:1.

11. Method according to claim 9, wherein said quantifiable antibody is capable of selective interaction with a peptide whose amino acid sequence consists of the sequence SEQ ID NO:8, 13 or 14.

12. Method according to claim 9, wherein said quantifiable antibody is a monoclonal antibody.

13. Method according to claim 2, wherein the bladder cancer is of grade 1 or 2.

14. Method according to claim 2, wherein said sample comprises tumor cells from said subject.

15. Method according to claim 2, wherein the evaluation of step a) is limited to the membranes of tumor cells of the sample.

16. Method according to claim 2, wherein the reference value of step b) corresponds to a reference sample having no detectable membranous PODXL protein in tumor cells.

17. Method according to claim 2, wherein said sample is a bladder tumor tissue sample.

18. Method according to claim 2, wherein step a) comprises:

aI) applying to said sample of step a) a quantifiable antibody capable of selective interaction with the PODXL protein to be evaluated, said application being performed under conditions that enable binding of the antibody to PODXL protein present in the sample; and aII) quantifying the antibody bound to said sample to evaluate said amount.

19. Method according to claim 18, wherein said quantifiable antibody is capable of selective interaction with a peptide whose amino acid sequence consists of the sequence SEQ ID NO:1.

20. Method according to claim 18, wherein said quantifiable antibody is capable of selective interaction with a peptide whose amino acid sequence consists of the sequence SEQ ID NO:8, 13 or 14.

21. Method according to claim 18, wherein said quantifiable antibody is a monoclonal antibody.

* * * * *

SEQUENCE LISTING

```
<160> NUMBER OF SEQ ID NOS: 14

<210> SEQ ID NO 1
<211> LENGTH: 138
<212> TYPE: PRT
<213> ORGANISM: Homo sapiens

<400> SEQUENCE: 1

Leu Pro Glu Thr Met Ser Ser Ser Pro Thr Ala Ala Ser Thr Thr His
1               5                   10                  15
```

```
Arg Tyr Pro Lys Thr Pro Ser Pro Thr Val Ala His Glu Ser Asn Trp
                20                  25                  30

Ala Lys Cys Glu Asp Leu Glu Thr Gln Thr Gln Ser Glu Lys Gln Leu
             35                  40                  45

Val Leu Asn Leu Thr Gly Asn Thr Leu Cys Ala Gly Gly Ala Ser Asp
 50                  55                  60

Glu Lys Leu Ile Ser Leu Ile Cys Arg Ala Val Lys Ala Thr Phe Asn
 65                  70                  75                  80

Pro Ala Gln Asp Lys Cys Gly Ile Arg Leu Ala Ser Val Pro Gly Ser
                 85                  90                  95

Gln Thr Val Val Val Lys Glu Ile Thr Ile His Thr Lys Leu Pro Ala
                100                 105                 110

Lys Asp Val Tyr Glu Arg Leu Lys Asp Lys Trp Asp Glu Leu Lys Glu
            115                 120                 125

Ala Gly Val Ser Asp Met Lys Leu Gly Asp
            130                 135

<210> SEQ ID NO 2
<211> LENGTH: 526
<212> TYPE: PRT
<213> ORGANISM: Homo sapiens

<400> SEQUENCE: 2

Met Arg Cys Ala Leu Ala Leu Ser Ala Leu Leu Leu Leu Leu Ser Thr
 1               5                  10                  15

Pro Pro Leu Leu Pro Ser Ser Pro Ser Pro Ser Pro Ser Pro Ser Gln
                20                  25                  30

Asn Ala Thr Gln Thr Thr Thr Asp Ser Ser Asn Lys Thr Ala Pro Thr
             35                  40                  45

Pro Ala Ser Ser Val Thr Ile Met Ala Thr Asp Thr Ala Gln Gln Ser
 50                  55                  60

Thr Val Pro Thr Ser Lys Ala Asn Glu Ile Leu Ala Ser Val Lys Ala
 65                  70                  75                  80

Thr Thr Leu Gly Val Ser Ser Asp Ser Pro Gly Thr Thr Thr Leu Ala
                 85                  90                  95

Gln Gln Val Ser Gly Pro Val Asn Thr Thr Val Ala Arg Gly Gly Gly
                100                 105                 110

Ser Gly Asn Pro Thr Thr Thr Ile Glu Ser Pro Lys Ser Thr Lys Ser
            115                 120                 125

Ala Asp Thr Thr Thr Val Ala Thr Ser Thr Ala Thr Ala Lys Pro Asn
            130                 135                 140

Thr Thr Ser Ser Gln Asn Gly Ala Glu Asp Thr Thr Asn Ser Gly Gly
145                 150                 155                 160

Lys Ser Ser His Ser Val Thr Asp Leu Thr Ser Lys Ala Glu
                165                 170                 175

His Leu Thr Thr Pro His Pro Ser Pro Leu Ser Pro Arg Gln Pro
            180                 185                 190

Thr Ser Thr His Pro Val Ala Thr Pro Thr Ser Ser Gly His Asp His
            195                 200                 205

Leu Met Lys Ile Ser Ser Ser Ser Thr Val Ala Ile Pro Gly Tyr
            210                 215                 220

Thr Phe Thr Ser Pro Gly Met Thr Thr Thr Leu Pro Ser Ser Val Ile
225                 230                 235                 240

Ser Gln Arg Thr Gln Gln Thr Ser Ser Gln Met Pro Ala Ser Ser Thr
```

```
                         245                 250                 255
Ala Pro Ser Ser Gln Glu Thr Val Gln Pro Thr Ser Pro Ala Thr Ala
                 260                 265                 270

Leu Arg Thr Pro Thr Leu Pro Glu Thr Met Ser Ser Pro Thr Ala
            275                 280                 285

Ala Ser Thr Thr His Arg Tyr Pro Lys Thr Pro Ser Pro Thr Val Ala
        290                 295                 300

His Glu Ser Asn Trp Ala Lys Cys Glu Asp Leu Glu Thr Gln Thr Gln
305                 310                 315                 320

Ser Glu Lys Gln Leu Val Leu Asn Leu Thr Gly Asn Thr Leu Cys Ala
                325                 330                 335

Gly Gly Ala Ser Asp Glu Lys Leu Ile Ser Leu Ile Cys Arg Ala Val
                340                 345                 350

Lys Ala Thr Phe Asn Pro Ala Gln Asp Lys Cys Gly Ile Arg Leu Ala
                355                 360                 365

Ser Val Pro Gly Ser Gln Thr Val Val Lys Glu Ile Thr Ile His
            370                 375                 380

Thr Lys Leu Pro Ala Lys Asp Val Tyr Glu Arg Leu Lys Asp Lys Trp
385                 390                 395                 400

Asp Glu Leu Lys Glu Ala Gly Val Ser Asp Met Lys Leu Gly Asp Gln
                405                 410                 415

Gly Pro Pro Glu Glu Ala Glu Asp Arg Phe Ser Met Pro Leu Ile Ile
            420                 425                 430

Thr Ile Val Cys Met Ala Ser Phe Leu Leu Leu Val Ala Ala Leu Tyr
            435                 440                 445

Gly Cys Cys His Gln Arg Leu Ser Gln Arg Lys Asp Gln Gln Arg Leu
        450                 455                 460

Thr Glu Glu Leu Gln Thr Val Glu Asn Gly Tyr His Asp Asn Pro Thr
465                 470                 475                 480

Leu Glu Val Met Glu Thr Ser Ser Glu Met Gln Glu Lys Lys Val Val
                485                 490                 495

Ser Leu Asn Gly Glu Leu Gly Asp Ser Trp Ile Val Pro Leu Asp Asn
            500                 505                 510

Leu Thr Lys Asp Asp Leu Asp Glu Glu Asp Thr His Leu
            515                 520                 525

<210> SEQ ID NO 3
<211> LENGTH: 558
<212> TYPE: PRT
<213> ORGANISM: Homo sapiens

<400> SEQUENCE: 3

Met Arg Cys Ala Leu Ala Leu Ser Ala Leu Leu Leu Leu Ser Thr
1               5                   10                  15

Pro Pro Leu Leu Pro Ser Ser Pro Ser Pro Ser Pro Ser Gln
            20                  25                  30

Asn Ala Thr Gln Thr Thr Thr Asp Ser Ser Asn Lys Thr Ala Pro Thr
            35                  40                  45

Pro Ala Ser Ser Val Thr Ile Met Ala Thr Asp Thr Ala Gln Gln Ser
        50                  55                  60

Thr Val Pro Thr Ser Lys Ala Asn Glu Ile Leu Ala Ser Val Lys Ala
65                  70                  75                  80

Thr Thr Leu Gly Val Ser Ser Asp Ser Pro Gly Thr Thr Leu Ala
                85                  90                  95
```

```
Gln Gln Val Ser Gly Pro Val Asn Thr Thr Val Ala Arg Gly Gly
            100                 105                 110

Ser Gly Asn Pro Thr Thr Thr Ile Glu Ser Pro Lys Ser Thr Lys Ser
            115                 120                 125

Ala Asp Thr Thr Thr Val Ala Thr Ser Thr Ala Thr Ala Lys Pro Asn
        130                 135                 140

Thr Thr Ser Ser Gln Asn Gly Ala Glu Asp Thr Thr Asn Ser Gly Gly
145                 150                 155                 160

Lys Ser Ser His Ser Val Thr Thr Asp Leu Thr Ser Thr Lys Ala Glu
                165                 170                 175

His Leu Thr Thr Pro His Pro Thr Ser Pro Leu Ser Pro Arg Gln Pro
            180                 185                 190

Thr Ser Thr His Pro Val Ala Thr Pro Thr Ser Ser Gly His Asp His
        195                 200                 205

Leu Met Lys Ile Ser Ser Ser Ser Thr Val Ala Ile Pro Gly Tyr
210                 215                 220

Thr Phe Thr Ser Pro Gly Met Thr Thr Thr Leu Leu Glu Thr Val Phe
225                 230                 235                 240

His His Val Ser Gln Ala Gly Leu Glu Leu Leu Thr Ser Gly Asp Leu
            245                 250                 255

Pro Thr Leu Ala Ser Gln Ser Ala Gly Ile Thr Ala Ser Ser Val Ile
        260                 265                 270

Ser Gln Arg Thr Gln Gln Thr Ser Gln Met Pro Ala Ser Ser Thr
        275                 280                 285

Ala Pro Ser Ser Gln Glu Thr Val Gln Pro Thr Ser Pro Ala Thr Ala
        290                 295                 300

Leu Arg Thr Pro Thr Leu Pro Glu Thr Met Ser Ser Ser Pro Thr Ala
305                 310                 315                 320

Ala Ser Thr Thr His Arg Tyr Pro Lys Thr Pro Ser Pro Thr Val Ala
                325                 330                 335

His Glu Ser Asn Trp Ala Lys Cys Glu Asp Leu Glu Thr Gln Thr Gln
            340                 345                 350

Ser Glu Lys Gln Leu Val Leu Asn Leu Thr Gly Asn Thr Leu Cys Ala
        355                 360                 365

Gly Gly Ala Ser Asp Glu Lys Leu Ile Ser Leu Ile Cys Arg Ala Val
370                 375                 380

Lys Ala Thr Phe Asn Pro Ala Gln Asp Lys Cys Gly Ile Arg Leu Ala
385                 390                 395                 400

Ser Val Pro Gly Ser Gln Thr Val Val Lys Glu Ile Thr Ile His
            405                 410                 415

Thr Lys Leu Pro Ala Lys Asp Val Tyr Glu Arg Leu Lys Asp Lys Trp
        420                 425                 430

Asp Glu Leu Lys Glu Ala Gly Val Ser Asp Met Lys Leu Gly Asp Gln
        435                 440                 445

Gly Pro Pro Glu Glu Ala Glu Asp Arg Phe Ser Met Pro Leu Ile Ile
        450                 455                 460

Thr Ile Val Cys Met Ala Ser Phe Leu Leu Leu Val Ala Ala Leu Tyr
465                 470                 475                 480

Gly Cys Cys His Gln Arg Leu Ser Gln Arg Lys Asp Gln Gln Arg Leu
                485                 490                 495

Thr Glu Glu Leu Gln Thr Val Glu Asn Gly Tyr His Asp Asn Pro Thr
        500                 505                 510

Leu Glu Val Met Glu Thr Ser Ser Glu Met Gln Glu Lys Lys Val Val
```

```
            515                 520                 525
Ser Leu Asn Gly Glu Leu Gly Asp Ser Trp Ile Val Pro Leu Asp Asn
        530                 535                 540

Leu Thr Lys Asp Asp Leu Asp Glu Glu Glu Asp Thr His Leu
545                 550                 555
```

```
<210> SEQ ID NO 4
<211> LENGTH: 10
<212> TYPE: PRT
<213> ORGANISM: Homo sapiens

<400> SEQUENCE: 4

Ala Ala Ser Thr Thr His Arg Tyr Pro Lys
1               5                   10

<210> SEQ ID NO 5
<211> LENGTH: 10
<212> TYPE: PRT
<213> ORGANISM: Homo sapiens

<400> SEQUENCE: 5

Thr Pro Ser Pro Thr Val Ala His Glu Ser
1               5                   10

<210> SEQ ID NO 6
<211> LENGTH: 5
<212> TYPE: PRT
<213> ORGANISM: Homo sapiens

<400> SEQUENCE: 6

Gln Thr Gln Ser Glu
1               5

<210> SEQ ID NO 7
<211> LENGTH: 15
<212> TYPE: PRT
<213> ORGANISM: Homo sapiens

<400> SEQUENCE: 7

Cys Gly Ile Arg Leu Ala Ser Val Pro Gly Ser Gln Thr Val Val
1               5                   10                  15

<210> SEQ ID NO 8
<211> LENGTH: 15
<212> TYPE: PRT
<213> ORGANISM: Homo sapiens

<400> SEQUENCE: 8

Ile His Thr Lys Leu Pro Ala Lys Asp Val Tyr Glu Arg Leu Lys
1               5                   10                  15

<210> SEQ ID NO 9
<211> LENGTH: 15
<212> TYPE: PRT
<213> ORGANISM: Homo sapiens

<400> SEQUENCE: 9

Asp Lys Trp Asp Glu Leu Lys Glu Ala Gly Val Ser Asp Met Lys
1               5                   10                  15

<210> SEQ ID NO 10
<211> LENGTH: 15
<212> TYPE: PRT
<213> ORGANISM: Homo sapiens
```

```
<400> SEQUENCE: 10

Ala Ala Ser Thr Thr His Arg Tyr Pro Lys Thr Pro Ser Pro Thr
1               5                   10                  15

<210> SEQ ID NO 11
<211> LENGTH: 15
<212> TYPE: PRT
<213> ORGANISM: Homo sapiens

<400> SEQUENCE: 11

Asn Trp Ala Lys Cys Glu Asp Leu Glu Thr Gln Thr Gln Ser Glu
1               5                   10                  15

<210> SEQ ID NO 12
<211> LENGTH: 15
<212> TYPE: PRT
<213> ORGANISM: Homo sapiens

<400> SEQUENCE: 12

Tyr Glu Arg Leu Lys Asp Lys Trp Asp Glu Leu Lys Glu Ala Gly
1               5                   10                  15

<210> SEQ ID NO 13
<211> LENGTH: 15
<212> TYPE: PRT
<213> ORGANISM: Homo sapiens

<400> SEQUENCE: 13

Gly Ala Ser Asp Glu Lys Leu Ile Ser Leu Ile Cys Arg Ala Val
1               5                   10                  15

<210> SEQ ID NO 14
<211> LENGTH: 15
<212> TYPE: PRT
<213> ORGANISM: Homo sapiens

<400> SEQUENCE: 14

Pro Ala Lys Asp Val Tyr Glu Arg Leu Lys Asp Lys Trp Asp Glu
1               5                   10                  15
```